United States Patent
Jaber et al.

(10) Patent No.: US 11,285,443 B2
(45) Date of Patent: Mar. 29, 2022

(54) COATED POROUS POLYMERIC MEMBRANES

(71) Applicant: ENTEGRIS, Inc., Billerica, MA (US)

(72) Inventors: Jad Ali Jaber, Westford, MA (US); Saksatha Ly, Lexington, MA (US); James Hamzik, Billerica, MA (US); Testu Kohyama, Tokyo (JP)

(73) Assignee: ENTEGRIS, INC., Billerica, MA (US)

( * ) Notice: Subject to any disclaimer, the term of this patent is extended or adjusted under 35 U.S.C. 154(b) by 33 days.

(21) Appl. No.: 16/304,900

(22) PCT Filed: May 26, 2017

(86) PCT No.: PCT/US2017/034649
§ 371 (c)(1),
(2) Date: Nov. 27, 2018

(87) PCT Pub. No.: WO2017/205722
PCT Pub. Date: Nov. 30, 2017

(65) Prior Publication Data
US 2020/0206691 A1    Jul. 2, 2020

Related U.S. Application Data

(60) Provisional application No. 62/342,392, filed on May 27, 2016.

(51) Int. Cl.
*B01D 67/00* (2006.01)
*B01D 69/02* (2006.01)
(Continued)

(52) U.S. Cl.
CPC ......... *B01D 67/0088* (2013.01); *B01D 69/02* (2013.01); *B01D 71/26* (2013.01);
(Continued)

(58) Field of Classification Search
CPC ........ B01D 69/02; B01D 71/26; B01D 71/78; B01D 71/82; B01J 20/267;
(Continued)

(56) References Cited

U.S. PATENT DOCUMENTS 6,379,551 B1    4/2002  Lee et al.
7,073,671 B2    7/2006  Charkoudian
(Continued)

FOREIGN PATENT DOCUMENTS

CN    1950406 A     4/2007
CN    105102127    11/2015
(Continued)

OTHER PUBLICATIONS

Agarwal, C. et al.; "Ionic Transport in polyelectrolyte-filled cation-exchange membranes"; Journal of Membrane Science (Impact Factor: 5.06). Nov. 2013; 446:125-131; Abstract Only.
(Continued)

*Primary Examiner* — Krishnan S Menon
(74) *Attorney, Agent, or Firm* — Entegris, Inc.

(57) ABSTRACT

The present disclosure provides a porous polymeric membrane that is coated with a cross-linked polymerized monomer. The coating on the porous polymeric membrane has a charge when it is immersed in an organic liquid. The coated porous polymeric membrane, a filter utilizing the membrane, and a method for treating an organic liquid used for photoresist with the coated porous polymeric membrane to remove metal contaminants from the organic liquid are disclosed.

13 Claims, 16 Drawing Sheets

(51) Int. Cl.
*B01D 71/26* (2006.01)
*B01D 71/78* (2006.01)
*B01D 71/82* (2006.01)
*B01J 20/26* (2006.01)
*B01J 20/28* (2006.01)
*B01J 20/32* (2006.01)
*C07C 45/78* (2006.01)
*C08J 5/22* (2006.01)
*G03F 7/027* (2006.01)

(52) U.S. Cl.
CPC ............ *B01D 71/78* (2013.01); *B01D 71/82* (2013.01); *B01J 20/267* (2013.01); *B01J 20/28035* (2013.01); *B01J 20/3208* (2013.01); *B01J 20/3282* (2013.01); *C07C 45/786* (2013.01); *C08J 5/2243* (2013.01); *G03F 7/027* (2013.01); *B01D 2323/30* (2013.01); *B01D 2325/14* (2013.01); *B01D 2325/16* (2013.01); *C08J 2333/26* (2013.01)

(58) Field of Classification Search
CPC .............. B01J 20/28035; B01J 20/3208; B01J 20/3282; C07C 45/786; C08J 5/2243; G03F 7/027
See application file for complete search history.

(56) References Cited

U.S. PATENT DOCUMENTS

| | | |
|---|---|---|
| 2010/0226823 A1 | 9/2010 | Rakhman et al. |
| 2010/0261801 A1* | 10/2010 | Weiss .................. B01D 67/0093 |
| | | 521/27 |
| 2014/0357740 A1 | 12/2014 | Yin et al. |
| 2015/0190760 A1 | 7/2015 | Singh et al. |

FOREIGN PATENT DOCUMENTS

| | | |
|---|---|---|
| EP | 1779922 | 6/2010 |
| JP | 2001017965 A | 1/2001 |
| JP | 2014173013 A | 9/2014 |
| JP | 2015203048 A | 11/2015 |
| WO | 1999/009091 | 2/1999 |
| WO | 2014050993 A1 | 4/2014 |
| WO | 2016/081729 | 5/2016 |

OTHER PUBLICATIONS

Pall Corporation Application Bulletin for Filter Selection for Optimized Photoresist Filtration; www.pall.com/micro; Sep. 2010.

* cited by examiner

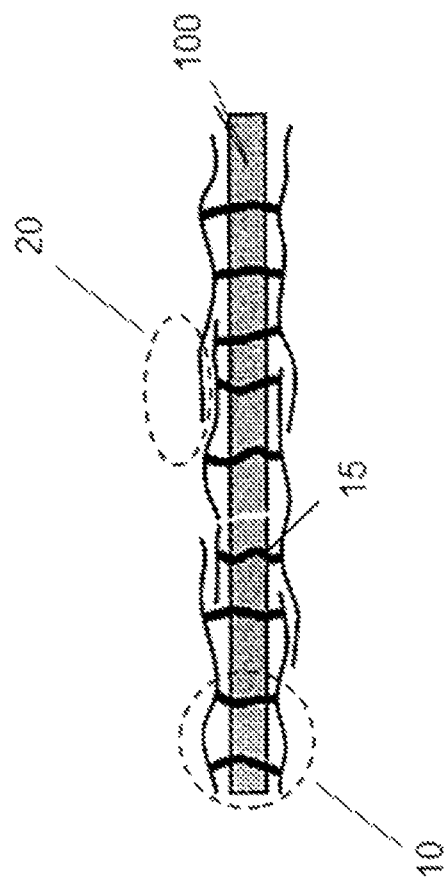

COATED POROUS POLYMERIC MEMBRANES

RELATED APPLICATIONS

This application is filed under the provisions of 35 U.S.C. § 371 claiming priority of International Patent Application No. PCT/US2017/034649 filed on May 26, 2017, which further claims the benefit of priority under 35 U.S.C. § 119 of U.S. Provisional Patent Application No. 62/342,392, filed 27 May 2016 incorporated herein by reference, in its entirety, for all purposes.

TECHNICAL FIELD

Versions of the disclosure relate to membranes and methods of using membranes to treat liquids. Particularly, the disclosure includes embodiments that relate to porous polymeric membranes coated with cross-linked monomers that are charged in an organic liquid and methods of using the membranes to remove metal contaminants from liquids.

BACKGROUND

Membranes have been used to remove metal contaminants from liquids in industries such as the micro-electronic industry. For instance, photoresist solutions with ultra low levels of metal ion contaminants are desirable for low wafer defectivity and higher yields during high volume manufacturing of integrated circuits. Cation exchange membranes (i.e. negatively charged membranes) are the industry standard for removing such metal contamination from photoresist solutions used in the production of microchips.

To remove metal contaminants, negatively charged membranes such as described in examples in U.S. Pat. No. 6,379,551 and publication METAL ION REMOVAL FROM PHOTORESIST SOLVENTS (Microlithography Conference) have described the removal of metal contaminants from organic solvents or mixed solvents. Most or many other membrane technologies target removing metals from aqueous solvent, not organic solvents, and or the membranes have not been modified with positive charge i.e. anion exchange membrane. See for example references such as U.S. Pat. No. 5,087,372.

Negatively charged or cation exchange membranes provide a way to remove metal contaminants from organic solvents due to favorable electrostatic interactions between opposite charges on membrane and metal contaminants. As discussed above, photoresist solutions with ultra low levels of metal ion contaminants are wanted for low wafer defectivity and higher yields for manufacturing integrated circuits. Existing cation exchange membranes however, are limited in their applicability to purify organic solvents and remove metal contaminants. More specifically they are limited in removing metal contaminants from water immiscible organic solvents due to limited selectivity.

Thus, need still exists for a device, membrane, and method of removing metal contaminants from organic solvents and specific types of organic solvents such as organic solvents used for photoresist and water immiscible organic solvents. Moreover, need still exists for materials that enable the removal of metal contaminants from organic liquids in general and specific types of organic solvents such as water immiscible organic solvents and organic solvents used for photoresist.

SUMMARY

The embodiments disclosed herein meets these and other needs by providing materials and methods of removing metal contaminants from organic liquids and specifically, water immiscible organic liquids.

Accordingly, one embodiment of the disclosure provides a method of removing metal contaminants from an organic liquid used for photoresist. The method includes passing an organic liquid used for photoresist through a porous polymeric membrane. The porous polymeric membrane includes a coating having a cross-linked polymerized monomer with a positive charge; and the organic liquid is a liquid that comprises a photoresist composition. The organic liquid has a lower concentration of the metal contaminants after passing thru the porous polymeric membrane.

A second aspect embodiment of the disclosure includes removing metal contaminants from an organic liquid. The method includes passing an organic liquid through a first porous polymeric membrane; and passing an organic liquid through a second porous polymeric membrane. The first porous polymeric membrane includes a coating having a cross-linked monomer with a positive charge. The second porous polymeric membrane includes a coating having a cross-linked polymerized monomer with a negative charge. The organic liquid has a lower concentration of the metal contaminants after passing thru the porous polymeric membranes.

A third aspect embodiment of the disclosure includes removing metal contaminants from an organic liquid. The method includes passing an organic liquid through a porous polymeric membrane. The porous polymeric membrane includes a coating having cross-linked polymerized monomers with positive and negative charges; and the organic liquid has a lower concentration of the metal contaminants after passing thru the porous membrane.

A fourth embodiment of the disclosure provides a filtration device for removing metal contaminants from an organic liquid used for photoresist. The filtration device includes a filter incorporating a porous polymeric membrane. The porous polymeric membrane includes a coating having one or more cross-linked polymerized monomers with a positive charge.

A fifth embodiment of the disclosure provides a filtration device for removing metal contaminants from an organic liquid. The filtration device includes a filter with a porous membranes. A first porous polymeric membrane in the filter includes a coating having a cross-linked polymerized monomer with a positive charge. A second porous polymeric membrane in the filter includes a coating having a cross-linked polymerized monomer with a negative charge.

A sixth embodiment of the disclosure provides a filtration device for removing metal contaminants from an organic liquid. The filtration device includes a filter incorporating a porous polymeric membrane. The porous polymeric membrane includes a coating having cross-linked polymerized monomers with positive and negative charges.

In some embodiments of the disclosure, positively charged polymerized monomers and/or negatively charged polymerized monomers can be cross-linked on separate porous polymeric membranes and the differently charged membranes layered together in a device.

In other embodiments of the disclosure, positively charged and negatively charged polymerized monomers can be mixed and cross-linked together on a porous polymeric membrane and used in a device.

In still other embodiments the polymerized monomers can comprise zwitterionic monomers which are cross-linked together on a porous polymeric membrane and used in a device.

BRIEF DESCRIPTION OF THE DRAWINGS

FIG. 1A is a schematic illustration of a coated porous polymeric membrane used for removing metal contaminants in accordance with an embodiment of the disclosure.

DETAILED DESCRIPTION

Figure 1B:
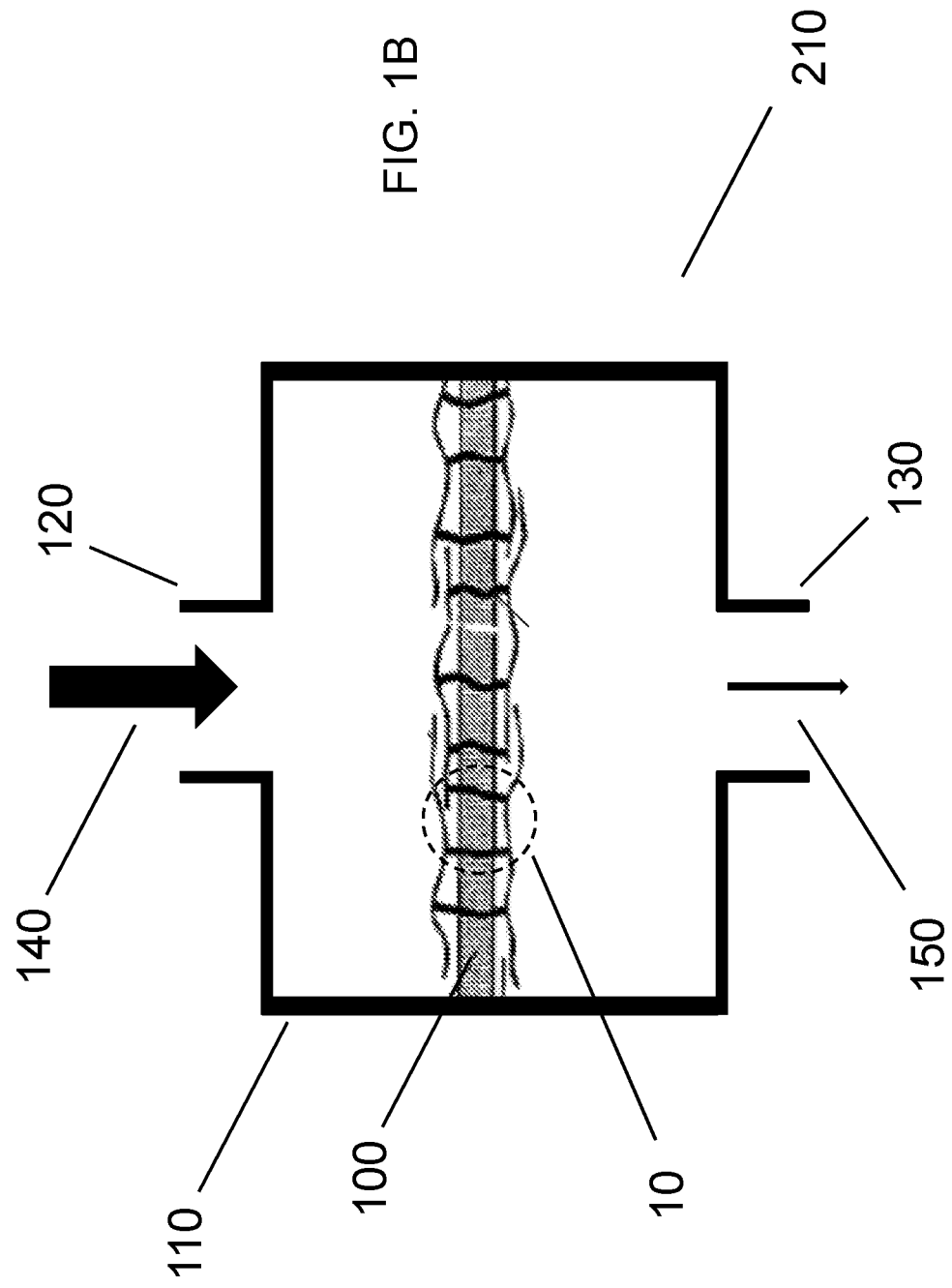
FIG. 1B is an illustration of a coated porous polymeric membrane in a device that can be used for removing metal contaminants in accordance with an embodiment of the disclosure.

In the following description, it is understood that terms such as "top," "bottom," "outward," "inward," and the like are words of convenience and are not to be construed as limiting terms. Reference will now be made in detail to exemplary embodiments of the disclosure, which are illustrated in the accompanying figures and examples. Referring to the drawings in general, it will be understood that the illustrations are for the purpose of describing a particular embodiments of the disclosure and are not intended to limit the same.

Whenever a particular embodiment of the disclosure is said to comprise or consist of at least one element of a group and combinations thereof, it is understood that the embodiment may comprise or consist of any of the elements of the group, either individually or in combination with any of the other elements of that group. Furthermore, when any variable occurs more than one time in any constituent or in a formula, its definition on each occurrence is independent of its definition at every other occurrence. Also, combinations of substituents and/or variables are permissible only if such combinations result in stable compounds.

An embodiment of the disclosure includes a filter device and a method of removing metal contaminants from an organic liquid by passing the organic liquid through a coated porous polymeric membrane. As shown in FIG. 1A, the porous polymeric membrane 100 includes a coating 10 having one or more polymerized monomers 20 with a charge in the organic liquid that are cross-linked by a cross-linker 15. The organic liquid has a lower concentration of the metal contaminants after passing through the coated porous membrane. The coated porous membrane could be placed in a filter housing.

FIG. 1B illustrates a filter device 210 which has a coated porous polymeric membrane 100 secured to a filter housing 110, the filter housing has a liquid inlet 120 and a liquid outlet 130. The porous polymeric membrane 100 includes a coating 10 having one or more polymerized monomers with a charge in the organic liquid that are cross-linked by a cross-linker.

Figure 1C:
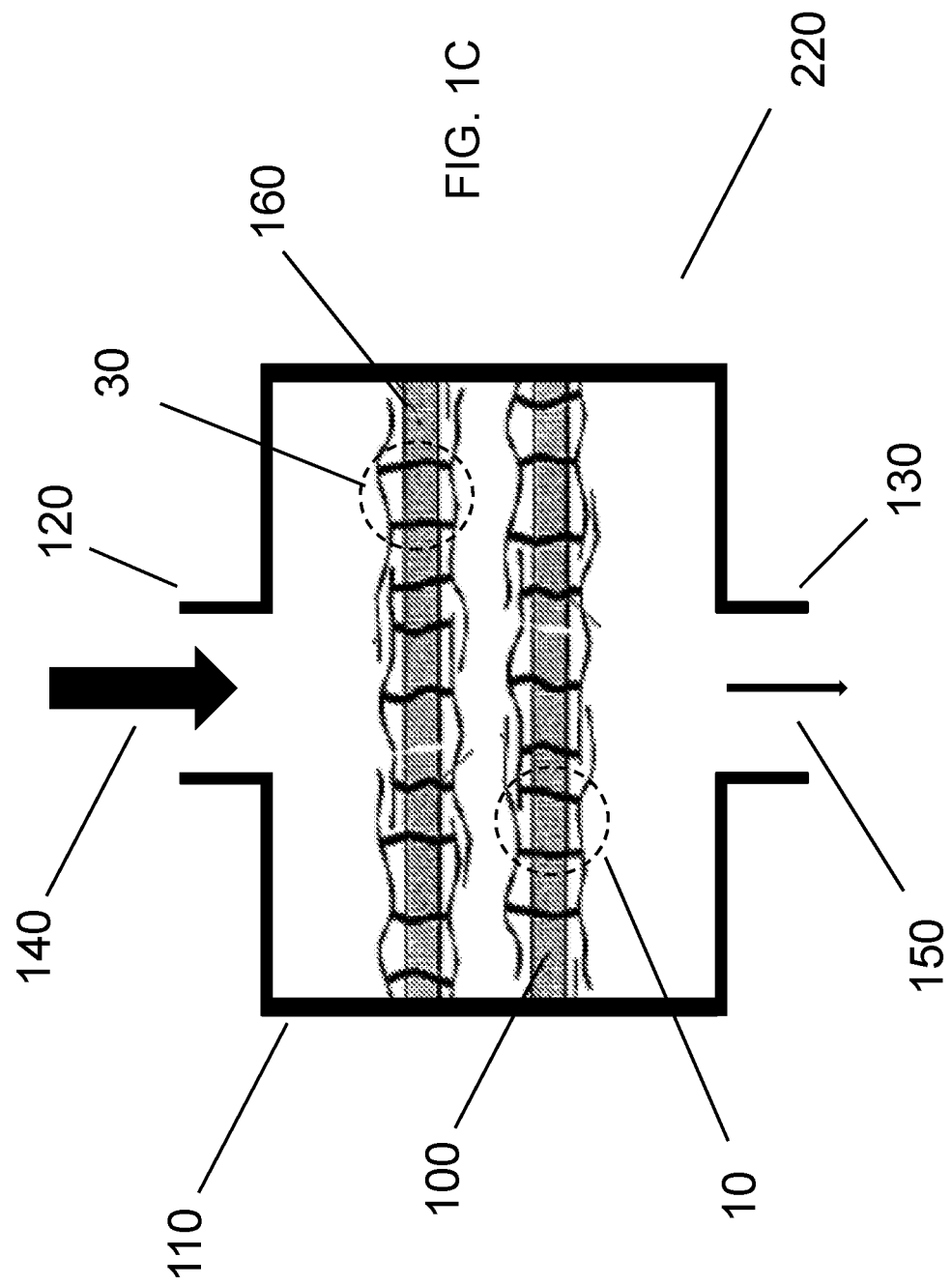
FIG. 1C is an illustration of multiple coated porous polymeric membranes in a device that can be used for removing metal contaminants in accordance with an embodiment of the disclosure.

FIG. 1C illustrates a filter device 220 which has at least two coated porous polymeric membranes 100 and 160 secured to a filter housing 110, the filter housing has a liquid inlet 120 and a liquid outlet 130. The porous polymeric membrane 100 includes a coating 10 having one or more polymerized monomers with a charge in the organic liquid that are cross-linked by a cross-linker and the porous polymeric membrane 160 includes a coating 30 having one or more polymerized monomers with a charge in the organic liquid that are cross-linked by a cross-linker.

In a particular embodiment, the organic liquid includes organic liquid used for photoresist or a photoresist composition. In another embodiment, the organic liquid is immiscible with water. In some versions, use of the term "metal" shall be understood to have the same meaning as the respective metal ion or a component of an ion complex unless stated otherwise. It should be appreciated that the metal also includes the reaction product of one or more ions with each other and the reaction product of the one or more metal ions and one or more solvents with each other. Metal contaminant is the presence of unwanted metals in an environment or material such liquid, making something less pure or suitable for intended purpose. In some versions, use of the term "metal" shall be understood to have the same meaning as the respective metal ion as a component of the ion complex unless stated otherwise. Metal contaminant can refer to neutral, negatively charged, or positively charged metal species and combinations thereof which may be present at equilibrium.

It should be appreciated that the methods of the disclosure include removing metal contaminants with various types of porous membranes and is not limited by the type membrane 100. Examples of porous membranes such as 100 or 160 can include but not limited to, polyethylene containing membranes, polysulfone containing membranes, polyether sulfone containing membranes, polyarylsulfone containing membranes, and PTFE membranes, either individually or in combinations of two or more thereof. A particular embodiment includes membranes comprising a polyolefin. Suitable polyolefins include, but are not limited to, polyethylene, high density polyethylene, ultra-high molecular weight polyethylene, and combinations of these. Suitable halocarbon polymers include, but are not limited to, polytetrafluoroethylene (PTFE), and polyvinylidene fluoride (PVDF), either individually or in combinations of two or more thereof. In a particular embodiment, the porous polymeric membrane includes a polyethylene based membrane referred to as ultra-high molecular weight polyethylene (UPE). UPE membranes are typically formed from a resin having a molecular weight greater than about 1,000,000 Daltons. In some embodiments the molecular weight of the UPE is in a range from about 2,000,000 Daltons to about 9,000,000 Daltons. In another embodiment, the molecular weight of the polyethylene membrane is in a range from about 1,000,000 Daltons to about 9,000,000 Daltons. In a particular embodiment, the molecular weight of the polyethylene membrane is in a range from about 1,500,000 Daltons to about 2,500,000 Daltons. In some instances, the porous polymeric membrane can have a bubble point between about 4 psi and 160 psi, when ethoxy-nonafluorobutane (or HFE-7200) is used as the wetting solvent. In one instance the porous polymeric membrane can be a polyethylene based membrane. It should be appreciated that although examples and embodiments herein are described with reference to UPE, the principles are not limited to polyethylene membranes. A person of ordinary skill in the art will also appreciate the porous polymeric membrane can be made of other suitable polymeric substances that include one or more polymerized monomers which are cross-linked to each other with cross linkers.

The porous polymeric membrane 100 can be any suitable porous membrane, which can be structurally amorphous, crystalline, or any suitable morphologic combination thereof. The porous polymeric membrane can be made of any suitable polymer such as, for example, polyolefins (including fluorinated polyolefins), polyamides, polyacrylates, polyesters, nylons, polysulfones (PS), polyethersulfones (PES), celluloses, polycarbonates, single polymers, copolymers, composites, and combinations thereof. The UPE membranes described herein can have a variety of geometric configurations, such as a flat sheet, a corrugated sheet, a pleated sheet, and a hollow fiber, among others. The porous polymeric membrane can have a pore structure that can be isotropic or anisotropic, skinned or unskinned, symmetric or asymmetric, any combination of these or can be a composite membrane including one or more retentive layers and one or more support layers. Furthermore, the coated porous membrane can be supported or unsupported by webs, nets, and cages, among others.

As shown in FIG. 1A, which is schematic of a membrane 100 used for removing metal contaminants, the porous polymeric membrane includes a coating 10 having one or more polymerized monomers 20 with a positive charge in a organic liquid. The coating 10 includes an organic backbone formed from the polymerized monomers. The coating 10 can include a crosslinker 15 and a monomer 20 or a co-polymer 20. In some embodiments the monomers have groups like alkyl ammonium groups that are positively charged in an organic solvent. It should be appreciated the plurality of polymerized monomers may differ from each other or may be the same with respect to various characteristic. Polymerization and cross-linking of the polymerizable monomer onto the porous membrane 100 substrate is effected so at least a portion and upto the entire surface of the porous membrane 100, including the inner pore surfaces of the porous membrane, is modified with a cross-linked polymer. It should be understood that the disclosure encompasses coating the porous membrane with as much of the surface of the membrane as desired, from greater than 0% to 100%, with cross-linked polymer composition.

In other embodiments of the coated porous polymeric membrane grafting can be used to modify the porous membrane and bond the polymerized monomer, co-polymer, cross-linker or a combination of these directly to the porous membrane material. In some other embodiments, a combination of techniques such as a portion is cross-linked and a portion is grafted can be used. Embodiments also encompass cross-linking a grafted portion. The cross-linking and grafting techniques encompass coating as much of the surface of the porous membrane as desired from greater than 0% to 100%.

Non-limiting examples of monomers 20 with a positive charge in an organic liquid that can be used in the coating 10 in embodiments of the disclosure can include, but are not limited to, 2-(dimethylamino)ethyl hydrochloride acrylate, [2-(acryloyloxy)ethyl]trimethylammonium chloride, 2-aminoethyl methacrylate hydrochloride, N-(3-aminopropyl) methacrylate hydrochloride, 2-(dimethylamino)ethyl methacrylate hydrochloride, [3-(methacryloylamino)propyl]trimethylammonium chloride solution, [2-(methacryloyloxy) ethyl]trimethylammonium chloride, acrylamidopropyl trimethylammonium chloride, 2-aminoethyl methacrylamide hydrochloride, N-(2-aminoethyl) methacrylamide hydrochloride, N-(3-aminopropyl)-methacrylamide hydrochloride, diallyldimethylammonium chloride, allylamine hydrochloride, vinyl imidazolium hydrochloride, vinyl pyridinium hydrochloride, and vinyl benzyl trimethyl ammonium chloride, either individually or in combinations of two or more thereof. In a particular embodiment, the monomer with positive charge includes acrylamido propyl trimethyl-ammonium chloride (APTAC). It should be appreciated that some monomers 20 with a positive charge listed above, comprise a quaternary ammonium group and are naturally charged in organic solvent while other monomers with a positive charge such as comprising primary, secondary and tertiary amines are adjusted to create charge by treatment with an acid. Monomers which can be positively charged in an organic solvent, either naturally or by treatment, can be polymerized and cross-linked with a cross-linker to form a coating on the porous membrane that is also positively charged when in contact with an organic solvent.

In an embodiment illustrated in FIG. 1A, the coating 10 on the porous polymeric membrane 100 includes a plurality of polymerized monomers 20 with a positive charge. It should be appreciated that embodiments of the disclosure can include a plurality of polymerized monomers 20 with a positive charge which differ from each other (co-polymer) or are the same (homo-polymer). In an embodiment, some of the pluralities of polymerized monomers with a positive charge are the same. In another particular embodiment, some of the plurality of polymerized monomers with a positive charge differ from each other. The plurality of polymerized monomers with a positive charge may have one or more characteristics which differ from each other or are similar. As shown in FIG. 1A, in a particular embodiment of the coating 10, one or more of the polymerized monomers are different from each other and form a co-polymer 20 with positive charges that are cross-linked with a cross-linker 15 to other polymerized monomers.

Examples of monomers 20 with negative charges in an organic liquid that can be used in the coating 10 can include, but are not limited to, 2-ethylacrylic acid, acrylic acid, 2-carboxyethyl acrylate, 3-sulfopropyl acrylate potassium salt, 2-propyl acrylic acid, 2-(trifluoromethyl)acrylic acid, methacrylic acid, 2-methyl-2-propene-1-sulfonic acid sodium salt, mono-2-(methacryloyloxy)ethyl maleate, 3-sulfopropyl methacrylate potassium salt, 2-acrylamido-2-methyl-1-propanesulfonic acid, 3-methacrylamido phenyl boronic acid, vinyl sulfonic acid, and vinyl phosphonic acid, either individually or combinations of two or more thereof. In a particular embodiment, the monomer with negative charge includes sulfonic acid. It should be appreciated that some monomers with a negative charge listed above, comprise a strong acid group and are naturally charged in organic solvent while other monomers with a negative charge comprising weak acids are adjusted to create charge by treatment with base. Monomers which are negatively charged in an organic solvent, either naturally or by treatment can be polymerized and cross-linked with a cross-linker 15 to form a coating on a porous membrane that is negatively charged in an organic solvent.

In an embodiment, the coating has a plurality of polymerized monomers 20 with negative charges. It should be appreciated that embodiments of the disclosure can include those with a plurality of monomers with negative charges which differ from each other or are the same. In an embodiment, the plurality of monomers with negative charges are the same. In another particular embodiment, the plurality of monomers with negative charges differ from each other. The plurality of monomers with negative charges may have one or more characteristics which differ from each other or are similar. As shown in FIG. 1A schematic membrane, in an embodiment of the coating, the one or more polymerized monomers 20 with negative charges that are cross-linked to other one or more polymerized monomers with negative charges. In another embodiment, the coating 10 can include a combination of polymerized monomers which are positively charged and negative charged that are cross-linked on the same membrane or respectively on separate membranes. In another embodiment, a porous polymeric membrane includes polymerized monomers 20 with positive charge that are cross-linked and another separate porous polymeric membrane includes polymerized monomers 20 with negative charges that are cross-linked. In another embodiment, the coating 10 with polymerized monomers having positive and negative charges are cross-linked and on the same porous polymeric membrane. In still other embodiments, the coating with polymerized monomers which are cross-linked includes monomers that are zwitterionic and have both positive and negative charges on the same monomer in an organic liquid.

A zwitterionic monomer has both a positive and negative charge in the same monomeric backbone. Non-limiting examples of zwitterionic monomers that can be polymerized and cross-linked on surfaces of a membrane include [3-(Methacryloylamino)propyl]dimethyl(3-sulfopropyl)ammonium hydroxide; [2-(Methacryloyloxy)ethyl]dimethyl-(3-sulfopropyl)ammonium hydroxide; 2-(Methacryloyloxy) ethyl 2-(Trimethylammonio)ethyl Phosphate; 1-(3-Sulfopropyl)-2-vinylpyridinium hydroxide; and combinations of these.

It should also be appreciated that methods of the disclosure include removing metal contaminants from a range of organic liquids, which can be liquids, either individually or in combinations of two or more thereof. Non limiting examples of organic liquids include cyclohexanone, isopentyl ether, PGMEA, Methyl isobutyl carbinol, N-butyl acetate, Methyl-2-hydroxyisobutyrate, and a mixed solution of propylene glycol monomethyl ether (PGME) and PGMEA (7:3 mixing ratio surface tension of 27.7 mN/m), and either individually or in combinations of two or more thereof. A particular embodiment includes organic liquids which are immiscible with water such as but not limited to cyclohexanone and PGMEA. In an embodiment, immiscible with water means soluble in water up to at 19.8 g per 100 ml water.

An embodiment of the disclosure includes removing metal contaminants from a combination of a plurality of organic liquids which differ from each other. A particular embodiment includes solvents used for photoresist. Examples of solvents used in photoresist include liquids such as but not limited to methyl-amyl ketone, ethyl-3-ethoxypropionate, propylene glycol methyletheracetate, methanol, and ethyl lactate, either individually or in combinations of two or more thereof.

The methods of the disclosure are not limited by a sequence or frequency or order of various acts or steps unless specified and may be repeated as desired.

Another embodiment includes removing metal contaminants from an organic liquid by passing an organic liquid through a plurality of porous polymeric membranes. In a particular embodiment, the first porous polymeric membrane includes a coating having a cross-linked polymerized monomer with a positive charge. The second porous polymeric membrane includes a coating having a cross-linked polymerized monomer with a negative charge. The organic liquid has a lower concentration of the metal contaminants after passing through the porous polymeric membranes. In a particular embodiment, the organic liquid includes liquids used for photoresist.

As discussed, the method is not limited by a sequence or order unless specified and may be repeated as desired. In another embodiment, the membrane with cross-linked monomers with negative charges is first membrane, and the membrane with the cross-linked monomers with positive charges is the second membrane. Furthermore, a combination of polymerized monomers 20 with positive and negative charges can be coated on the porous polymeric membrane 100. In another embodiment, the coating 10 with polymerized monomers 20 having positive and negative charges are on the same membrane 100. In an embodiment, the first membrane in a two layer membrane stack can include a coating 10 with polymerized monomers 20 having positive and negative charges on the same membrane 100. In another embodiment, the second membrane in a two layer membrane stack can include a coating 10 with polymerized monomers having positive and negative charge on the same membrane 100. As discussed, sequence or frequency or order may be altered unless specified. It should be appreciated that the first and second membranes 100 may effectively remove metal contaminants which differ from each other or at differing efficiency.

Another embodiment includes a method of removing metal contaminants from an organic liquid by passing an organic liquid through a porous polymeric membrane 100 having a plurality of layers. The porous polymeric membrane includes first layer and second layer. The first layer includes a coating 10 having one or more cross-linked polymerized monomers 20 with a positive charge. The second layer includes a coating having one or more cross-linked polymerized monomers 20 with a negative charge. The organic liquid has a lower concentration of the metal contaminants after passing thru the porous polymeric membrane 100. In a particular embodiment, the organic liquid includes liquids used for photoresist. A combination of polymerized monomers with positive and negative charges can be coated on the layers of the polymeric membrane 100. It should be appreciated that different layers of a membrane 100 and in a device 200 may effectively remove metal contaminants which differ from each other or at differing efficiency.

In an embodiment, metal contaminants removed include such as but are not limited to Li, Na, Mg, Al, K, Ca, Ti, V, Cr, Mn, Fe, Co, Ni, Cu, Zn, Sr, Mo, Ag, Cd, Sn, Ba, and Pb, either individually or in combinations of two or more thereof. In another embodiment, metal contaminants are removed such as Al, Ca, Cr, Cu, Fe, Pb, Mg, Mn, Ni, K, Na, Sn, Ti, and Zn, either individually or in combinations of two or more thereof. In a particular embodiment, metal contaminants are removed such as Fe, Ni, Cr, Cu, and Al, either individually or in combinations of two or more thereof. In an embodiment, metal contaminants are removed such as Fe, Ni, and Cr, either individually or in combinations of two or more thereof. In an embodiment, metal contaminant removal efficiency of metals, such as Al, Ca, Cr, Cu, Fe, Pb, Mg, Mn, Ni, K, Na, Sn, Ti, and Zn combined, from water immiscible organic liquid after passing the water immiscible organic liquid thru the porous membrane is about 95% for removing metal contaminants from organic liquid immiscible with water. In the examples provided infra, a device with 1000 cm$^2$ membrane area was challenged with 1200 ml of solution of respective liquid. In a particular embodiment, metal contaminant removal efficiency is about 94%, 93%, 92%, 91, 90%, and 85% and 80% as detailed in Table 1 infra. In other words, the metal contaminant concentration in the organic liquid feed stream for one or more of the metal species listed above is reduced after passing through one or more of the coated porous membranes by about 94%, 93%, 92%, 91, 90%, and 85% and 80% of the initial feed concentration. In some embodiments the metal contaminant concentration in the organic liquid feed stream is 150 parts per billion (ppb$_{v/v}$) or less and the metal contaminant removal is measured by passing the organic liquid feed stream through a device including 1000 cm$^2$ of coated porous membrane as described herein at a flow rate of 60 milliliters per minute (ml/min) and measuring the treated effluent organic liquid.

In an embodiment, the total concentration of metal contaminants in the organic liquid after passing thru the porous membrane is less than 20 ppb$_{v/v}$. In another embodiment, the concentration of total metal contaminants in the organic liquid after passing thru the porous membrane is less than about 19 ppb$_{v/v}$. In a particular embodiment, concentration of total metal contaminants in the organic liquid after passing thru the porous membrane is less than about 18 ppb$_{v/v}$. In other embodiments, concentration of total metal contaminants is less than about 17 ppb$_{v/v}$, less than about 16 ppb$_{v/v}$, less than about 15 ppb$_{v/v}$, less than about 14 ppb$_{v/v}$, less than about 13 ppb$_{v/v}$, less than about 12 ppb$_{v/v}$, less than about 11 ppb$_{v/v}$, and less than about 10 ppb$_{v/v}$. In some embodiments the organic liquid is water immiscible.

In a particular embodiment, metal contaminant removal efficiency of Fe contaminants from the organic liquid after passing through a device with a 1000 cm$^2$ sample of the coated cross-linked monomer on a porous membrane is at least 95% [after 1200 mL liquid treated by the device] for removing metal contaminants from organic liquid. In another embodiment, Fe contaminant removal efficiency is about 94%, 93%, 92%, 91, 90%, and 85% and 80%. In an embodiment, the concentration of Fe contaminants in the organic liquid after passing thru the porous membrane is less than about 0.7 parts per billion by volume (ppb$_{v/v}$). In another embodiment, the concentration of Fe contaminants in the organic liquid after passing thru the porous membrane is less than about 0.6 ppb$_{v/v}$. In a particular embodiment, the concentration of Fe contaminants in the organic liquid after passing thru the porous membrane is about 0.5 ppb$_{v/v}$. In other embodiments, concentration of Fe contaminants is less than about 0.5 ppb$_{v/v}$ and less than about 0.4 ppb$_{v/v}$. In some embodiments, the organic liquid is water immiscible.

In another particular embodiment, metal contaminant removal efficiency of Ni contaminants from organic liquid after passing through a device with a 1000 cm² sample of the coated cross-linked monomer on a porous membrane is at least 95% [after 1200 mL liquid treated by the device] for removing metal contaminants from organic liquid. In other embodiments, Ni contaminant removal efficiency is about 94%, 93%, 92%, 91, 90%, and 85% and 80%. In an embodiment, the concentration of Ni contaminants in the organic liquid after passing thru the porous membrane is about 0.5 $ppb_{v/v}$. In another embodiment, the concentration of Ni contaminants in the organic liquid after passing thru the porous membrane is less than about 0.4 $ppb_{v/v}$. In a particular embodiment, the concentration of Ni contaminants in the organic liquid after passing thru the porous membrane is about 0.3 $ppb_{v/v}$. In other embodiments, concentration of Ni contaminants is less than about 0.3 $ppb_{v/v}$ and less about 0.2 $ppb_{v/v}$. In some embodiments, the organic liquid is water immiscible.

In yet another embodiment, metal contaminant removal efficiency of Cr from organic liquid after passing through a device with a 1000 cm² sample of the coated cross-linked monomer on a porous membrane is at least 95% [after 1200 mL liquid treated by the device] for removing metal contaminants from organic liquid. In another embodiment, Cr contaminant removal efficiency is about 94%, 93%, 92%, 91, 90%, and 85% and 80%. In an embodiment, the concentration of Cr contaminants in the organic liquid after passing thru the porous membrane is about 2.0 $ppb_{v/v}$. In another embodiment, the concentration of Cr contaminants in the organic liquid after passing thru the porous membrane is less than about 1.9 $ppb_{v/v}$. In a particular embodiment, the concentration of Cr contaminants in the organic liquid after passing thru the porous membrane is about 1.8 $ppb_{v/v}$. In other embodiments, concentration of Cr contaminants is less than about 1.7 $ppb_{v/v}$, less than about 1.6 $ppb_{v/v}$, and less than about 1.5 $ppb_{v/v}$. In some embodiments, the organic liquid is water immiscible.

In yet another embodiment, metal contaminant removal efficiency of Al from organic liquid after passing through a device with a 1000 cm² sample of the coated cross-linked monomer on a porous membrane is at least 95% [after 1200 mL liquid treated by the device] for removing metal contaminants from organic liquid. In other embodiment, Al contaminant removal efficiency is about 94%, 93%, 92%, 91, 90%, and 85% and 80%. In an embodiment, the concentration of Al contaminants in the organic liquid after passing thru the porous membrane is less than about 0.4 $ppb_{v/v}$. In another embodiment, the concentration of Al contaminants in the organic liquid after passing thru the porous membrane is less than about 0.3 $ppb_{v/v}$. In a particular embodiment, the concentration of Al contaminants in the organic liquid after passing thru the porous membrane is about 0.2 $ppb_{v/v}$. In some embodiments the organic liquid is water immiscible.

In another embodiment, metal contaminant removal efficiency of Cu from the organic liquid after passing through a device with a 1000 cm² sample of the coated cross-linked monomer on a porous membrane is at least 95% [after 1200 mL liquid treated by the device] for removing metal contaminants from organic liquid. In other embodiments, Cu contaminant removal efficiency is about 94%, 93%, 92%, 91, 90%, and 85% and 80%. In a particular embodiment, the concentration of Cu contaminants in the organic liquid after passing thru the porous membrane is less than about 0.6 $ppb_{v/v}$. In another embodiment, the concentration of Cu contaminants in the organic liquid after passing thru the porous membrane is less than about 0.5 $ppb_{v/v}$. In a particular embodiment, the concentration of Cu contaminants in the organic liquid after passing thru the porous membrane is less than about 0.4 $ppb_{v/v}$.

The amount of negatively charged groups in the coatings on the porous polymeric membranes in embodiments of the disclosure is related to the amount of methylene blue dye (available from Sigma) that binds to the membrane. To determine the methylene blue dye binding capacity by a membrane sample, a 47 mm diameter sample of the coated membrane can be soaked in a beaker containing a solution containing 0.00075 weight % of the dye for 5 minutes with continuous mixing at room temperature. The membrane disk can then be then removed and the absorbance of the dye solution measured using a Cary spectrophotometer (Agilent Technologies) operating at a wavelength of 666 nanometers (nm) and compared to the absorbance of starting solution (before membrane soaking). Since the dye is cationic in nature it bound to the negatively charged membrane. In embodiments of porous polymeric membranes comprising cross-linked polymerized negatively charged monomers, the methylene blue dye binding can range from 10 $\mu g/cm^2$ to 50 $\mu g/cm^2$.

The amount of positively charged groups in the coatings on the porous polymeric membranes in embodiments of the disclosure is related to the amount of Ponceau-S dye (available from Sigma) dye that binds to the membrane. To determine the Ponceau-S dye binding capacity by a membrane sample, a 47 mm diameter sample of the coated membrane can be soaked in a beaker containing 0.002 weight % Ponceau-S dye (Sigma) for 5 minutes with continuous mixing at room temperature. The membrane disk can then be removed and the absorbance of the dye solution measured using a Cary spectrophotometer (Agilent Technologies) operating at a wavelength of 512 nm and compared to the absorbance of starting solution (before membrane soaking). Because the dye is anionic in nature, the dye is bound to the positively charged membrane. In embodiments of porous polymeric membranes comprising cross-linked polymerized positively charge monomers, the Ponceau-S dye binding can range from 10 $\mu g/cm^2$ to 80 $\mu g/cm^2$.

The charge density of the porous polymeric membranes comprising cross-linked polymerized negatively charge monomers can be determined by titration of HCl conditioned membrane samples with 0.001 M NaOH as described herein. The charge density of the negatively charged membrane in embodiments of the disclosure may range from about 0.5 to about 20 $meq/m^2$. In some embodiments, the negatively charged membrane can have a charge density as determined by the above titration procedure of from about 2.0 $meq/m^2$ to 15 $meq/m^2$; in other embodiments the charge density can range from 4.0 $meq/m^2$ to 15 $meq/m^2$; from 5 $meq/m^2$ to 13 $meq/m^2$; from 6 $meq/m^2$ to 12 $meq/m^2$; and from 7.0 $meq/m^2$ to 9 $meq/m^2$. Higher charge densities provide greater contaminant binding capacity.

The charge density of the porous polymeric membranes comprising cross-linked polymerized positively charge monomers can be determined by titration of NaOH conditioned membrane samples with 0.001 M HCl as described herein. The charge density of the positively charged membrane in embodiments of the disclosure may range from about 0.5 $meq/m^2$ to about 20 $meq/m^2$. In some embodiments, the positively charged membrane can have a charge density as determined by this titration procedure can range from about 2.0 $meq/m^2$ to 15 $meq/m^2$; in other embodiments the charge density can range from: 4.0 $meq/m^2$ to 15 $meq/m^2$; from 5 $meq/m^2$ to 13 $meq/m^2$; from 6 $meq/m^2$ to 12 $meq/m^2$; from 7.0 $meq/m^2$ to 9 $meq/m^2$; from 5.0 $meq/m^2$ to 7 meq/m$^2$; and from 4.0 meq/m$^2$ to 6 meq/m$^2$. Higher charge densities provide greater contaminant binding capacity.

It should be appreciated that first and second coated porous polymeric membranes as disclosed herein and a device containing these may effectively remove metal contaminants which differ from each other. In some embodiments the organic liquid is water immiscible.

Device

Another embodiment of the disclosure provides a filtration device 210 as shown in FIG. 1B. The filtration device 210 includes a filter incorporating a porous polymeric membrane 100. The porous polymeric membrane 100 includes a coating having a cross-linked polymerized monomer with a charge. Embodiments of the filtration device include coated porous polymeric membranes with positively charged monomers, negatively charged monomers, those with positively charged monomer and negatively charged monomers mixed together, those with zwitterionic monomers, and those that combine one or more charged monomers on two or more separate porous polymeric membrane layers (see FIG. 1C and device 220). In an embodiment, organic liquid has a lower concentration of metal contaminants after passing through the porous membrane. In a particular embodiment, the organic liquid includes water immiscible organic liquid. In another particular embodiment, the organic liquid includes organic liquid used for photoresist.

Another embodiment of the filtration device 220 includes a filter as shown in FIG. 1C incorporating a plurality of membranes 100 and 160. A first porous polymeric membrane 100 includes a coating 10 having a cross-linked polymerized monomer with a positive charge. A second porous polymeric membrane 160 includes a coating 30 having a cross-linked polymerized monomer with a negative charge. In an embodiment, organic liquid has a lower concentration of metal contaminants after passing through the porous membrane. In a particular embodiment, the organic liquid includes water immiscible organic liquid. In another particular embodiment, the organic liquid includes organic liquid used for photoresist.

As discussed, embodiments are not limited by a sequence or order unless specified and may be repeated as desired. In another embodiment, the membrane with cross-linked monomers with negative charges is first membrane, and the membrane with the cross-linked monomers with positive charges is the second membrane. Furthermore, a combination of polymerized monomers 20 with positive and negative charges can be coated on the polymeric membrane 100. It should be appreciated that the first and second membranes 100 may effectively remove metal contaminants which differ from each other or at differing efficiency.

Another embodiment of the filtration device 220 includes a filter incorporating one or more polymeric porous membranes 100, and 160. In the illustrated and non-limiting embodiment in FIG. 1C, the device 220 has porous polymeric membrane including a first layer 110 and second layer 160. The first layer includes a coating 10 having one or more cross-linked polymerized monomers with a positive charge. The second layer includes a coating 30 having one or more cross-linked polymerized monomers with a negative charge. The organic liquid has a lower concentration of the metal contaminants after passing through the coated porous polymeric membranes 100 and 160. In a particular embodiment, the organic liquid includes a liquid used for photoresist. A combination of polymerized monomers with positive and negative charges can be coated on the layers of the polymeric membrane 100. It should be appreciated that different layers of a membrane in the device 220 may effectively remove metal contaminants which differ from each other or at differing efficiency. Order of the layers does not matter and is not restricted unless specified.

As discussed supra, non-limiting examples of monomers with positive charges include 2-(dimethylamino)ethyl hydrochloride acrylate, [2-(acryloyloxy) ethyl]trimethylammonium chloride, 2-aminoethyl methacrylate hydrochloride, N-(3-aminopropyl) methacrylate hydrochloride, 2-(dimethylamino)ethyl methacrylate hydrochloride, [3-(methacryloylamino)propyl]trimethylammonium chloride solution, [2-(methacryloyloxy)ethyl]trimethylammonium chloride, acrylamidopropyl trimethylammonium chloride, 2-aminoethyl methacrylamide hydrochloride, N-(2-aminoethyl) methacrylamide hydrochloride, N-(3-aminopropyl)-methacrylamide hydrochloride, diallyldimethylammonium chloride, allylamine hydrochloride, vinyl imidazolium hydrochloride, vinyl pyridinium hydrochloride, and vinyl benzyl trimethyl ammonium chloride, either individually or in combinations of two or more thereof.

In a particular embodiment, the monomer with positive charge that can be used in a coating includes acrylamido propyl trimethylammonium chloride (APTAC).

In an embodiment, the coating 10 includes a plurality of polymerized monomers with positive charges. It should be appreciated that embodiments of the disclosure include a plurality of polymerized monomers with positive charges which differ from each other or are the same. In an embodiment, some of the plurality of polymerized monomers 20 with positive charges are the same. In another particular embodiment, some of the plurality of polymerized monomer with positive charges differ from each other. The plurality of polymerized monomers 20 with positive charges may have one or more characteristics which differ from each other or are similar. As shown in FIG. 1A, in a particular embodiment, one or more monomers with positive charges can be cross-linked to other one or more monomers.

As also discussed supra, examples of monomers with negative charges include such as but not limited to 2-ethylacrylic acid, acrylic acid, 2-carboxyethyl acrylate, 3-sulfopropyl acrylate potassium salt, 2-propyl acrylic acid, 2-(trifluoromethyl)acrylic acid, methacrylic acid, 2-methyl-2-propene-1-sulfonic acid sodium salt, mono-2-(methacryloyloxy)ethyl maleate, 3-sulfopropyl methacrylate potassium salt, 2-acrylamido-2-methyl-1-propanesulfonic acid, 3-methacrylamido phenyl boronic acid, vinyl sulfonic acid, and vinyl phosphonic acid, either individually or combinations of two or more thereof.

In a particular embodiment, the monomer with negative charge that can be used in a coating includes vinyl sulfonic acid or a salt thereof.

In an embodiment, the plurality of polymerized monomers 20 includes monomers with negative charges. It should be appreciated that embodiments of the disclosure include a plurality of polymerized monomers 20 with negative charges which differ from each other or are the same. In an embodiment, the plurality of monomers polymerized with negative charges are the same. In another particular embodiment, the plurality of polymerized monomers 20 with negative charges differ from each other. The plurality of polymerized monomers 20 with negative charges may have one or more characteristics which differ from each other or are similar. Monomers with negative charges can be cross-linked to other monomers with other charges or same charges.

In an embodiment, the plurality of polymerized monomers include zwitterionic monomers. Polymerized zwitterionic monomers 20 can be cross-linked or grafted to the porous polymeric membrane 100. It should be appreciated that embodiments of the disclosure include a plurality of polymerized zwitterionic monomers 20 which differ from each other or are the same. In an embodiment, the plurality of zwitterionic polymerized monomers are the same. In another particular embodiment, the plurality of polymerized zwitterionic monomers 20 differ from each other. The plurality of polymerized zwitterionic monomers 20 may have one or more characteristics which differ from each other or are similar.

A zwitterionic monomer has both a positive and negative charge in the same monomeric backbone. Examples of zwitterionic monomers that can be grafted or cross-linked to the porous polymeric membrane in embodiments of the disclosure include [3-(Methacryloylamino)propyl]dimethyl (3-sulfopropyl)ammonium hydroxide; [2-(Methacryloyloxy)ethyl]dimethyl-(3-sulfopropyl)ammonium hydroxide; 2-(Methacryloyloxy)ethyl 2-(Trimethylammonio)ethyl Phosphate; and 1-(3-Sulfopropyl)-2-vinylpyridinium hydroxide either individually or combinations of two or more thereof.

EXAMPLES

For illustration and not limitation, polymerization and cross-linking of the polymerizable monomer onto the porous membrane 100 substrate can be effected so that a select portion or the entire surface of the porous membrane 100, including the inner surfaces of the porous membrane, is modified with a cross-linked polymer. It should be understood that various embodiments of the coated porous polymeric membrane encompasses cross-linking as much of the surface of the membrane as desired from greater than 0% to 100%. It should also be understood that embodiments also encompass other technique such as grafting and a combination of techniques such as a portion is cross-linked and a portion is grafted. Embodiments also encompass cross-linking a grafted portion.

A reagent bath comprised of: (1) at least one polymerizable monomer which is ethylenically unsaturated and has at least one charged monomer group, (2) a polymerization initiator, if needed, and (3) a cross-linking agent in a polar solvent such as a water soluble solvent for these three constituents, is contacted with the porous polymeric membrane substrate under conditions to effect polymerization and crosslinking of the monomer and deposition of the resulting cross-linked polymer onto the porous polymeric membrane substrate. Even though the solvent is a polar solvent, the requisite degree of membrane surface modification may be and is obtained. When the monomer is di-functional or has higher functionality, an additional cross-linking agent is not needed but may be used. Representative suitable polar solvents include solvents having a dielectric constant above 25 at room temperature such as polyols including 2-methyl-2,4-pentanediol, 2,4 pentanedione, glycerine or 2,2'-thiodiethanol; amides such as formamide, dimethyl formamide, dimethyl acetamide; alcohols such as methanol, or the like; and nitro substituted aromatic compounds including nitrobenzene, 2-furaldehyde, acetonitrile, 1-methyl pyrrolidone or the like. The particular solvent is chosen to solublize the cross-linking agent, the monomer and the initiator, if present.

Suitable initiators and cross-linking agents for the monomers described above can be used. For example, when utilizing charged alkyl groups as the polymerizable monomer, suitable photopolymerization initiators include benzophenone, 4-(2-hyroxyethoxy)phenyl-(2-hydroxy-2-propyl) ketone, azoisopropane or 2,2-dimethoxy-2-phenylacetophenone or the like. Suitable thermal initiators include organic peroxides such as dibenzoyl peroxide, t-butylhydroperoxide, cumylperoxide or t-butyl perbenzoate or the like and azo compounds such as azobisisobutyronitrile (AIBN) or 4,4,'-azobis(4-cyanovaleric acid) or the like. Representative suitable cross-linking agents include 1,6-hexanediol diacrylate, tetraethylene glycol diacrylate; 1,1,1-trimethylolpropane triacrylate or the like; N,N'-methylene bisacrylamide or the like, either individually or combinations of two or more thereof.

Generally, the polymerizable monomer is present in the reactant solution at a concentration between about 2% and about 20%, preferably between about 5% and about 10% based upon the weight of the total solution. The cross-linking agent is present in an amount of between about 2% and about 10% by weight, based upon the weight of the polymerizable monomer. Greater amounts of cross-linking agents can be used. The polymerization initiator is present in an amount of between about 1% and about 10% by weight, based upon the weight of the polymerizable monomer. As noted above, the cross-linking agent can be utilized without the monomer and thereby functions as the polymerizable monomer.

Polymerization and cross-linking is effected by exposing the monomer reaction system to ultraviolet (UV) light, thermal sources or ionizing radiation. The polymerization and crosslinking is effected in an environment where oxygen does not inhibit polymerization or crosslinking. The process is conveniently effected by dipping the membrane substrate in the solution containing the monomer, crosslinking agent, and the initiator, sandwiching the membrane between two ultraviolet light transparent sheets, such as polyethylene, or in a blanket of an inert gas such as nitrogen and exposing to UV light. The process can be effected continuously and the desired cross-linked coating is formed after UV exposure is initiated. By controlling the reactant concentrations and UV exposure, as set forth above, a composite membrane is produced which is nonplugged and has essentially the same porous configuration as the membrane substrate.

Bubble Point

The porosimetry bubble point test method measures the pressure required to push air through the wet pores of a membrane. Generally the higher the pressure, the smaller the pore size of the membrane. The test was performed by mounting a 47 mm disk of a dry membrane sample in a holder with the tight side (e.g., having smaller pores in an asymmetric membrane) of the membrane facing down. The holder is designed in a way to allow the operator to place a small volume of liquid on the upstream side of the membrane. The dry air flow rate of the membrane is measured first by increasing the air pressure on the upstream side of the membrane to 30 psi. The pressure is then released back to atmospheric pressure and a small volume of isopropyl alcohol. (IPA) (Sigma, USA) is placed on the upstream side of the membrane to wet the membrane. The wet air flow rate is then measured by increasing the pressure again to 30 psi. The bubble point of the membrane is measured from the pressure required to displace IPA from the pores of the IPA-wet membrane. This critical pressure point is defined as the pressure at which a first non-linear increase of wet air flow is detected by the flow meter. The range of observed IPA bubble point for porous membranes used in this application was 7-11 pounds per square inch (psi).

IPA Flow Time

Membrane IPA flow time was determined by cutting membranes into 47 mm disks and wetting with IPA before placing the disk in a filter holder with a reservoir for holding a volume of IPA. The reservoir is connected to a pressure regulator. IPA was flowed through the membrane under 14.2 psi (pounds per square inch) differential pressure. After equilibrium was achieved, the time for 500 ml of IPA to flow through the membrane was recorded.

Figure 4:
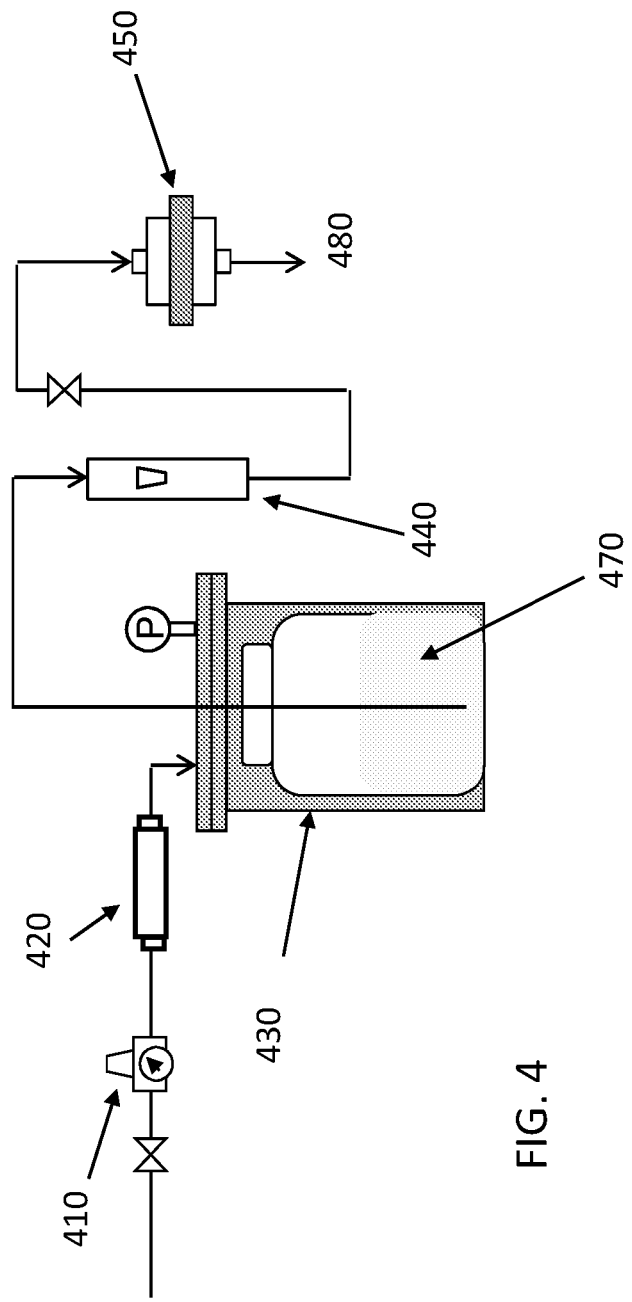
FIG. 4 is a schematic of diagram of a testing line for removing metal contaminants in accordance with an embodiment of the disclosure.

FIG. 4 is a schematic of diagram of a testing line for removing metals from an organic liquid in accordance with an embodiment of the disclosure. The testing line can include a pressure reducing valve 410 in-line with a gas purifier and or particle filter 420 to purify the gas used to pressure dispense test organic liquid 470 contained in pressure vessel 430. The test organic liquid 470 can be spiked with a metals standard like CONOSTAN S-12 Standard (SCP science, oil based 12 metal standard, 10 ppm total concentration) to create the metals challenge in the liquid 470. The volume and flow rate of the spiked organic liquid can be determined using flow meter 440 and by collection of filtrate 480 after passing through one or more test coated porous polymeric membranes in membrane test holder or disposable filter 450. The method is not limited by the order or frequency of the steps unless expressly noted. It should be appreciated method includes repeating steps at desired frequency and intervals unless specified.

Fill the tank with the feed (challenge) solution of organic liquid.

Pump challenge solution of organic liquid through the device at 60 ml/min flow rate for 20 min. Collect filtrate.

Measure metal concentration of the feed and filtrate solutions of the organic liquid using atomic absorption spectroscopy or ICP-MS. Calculate metal removal efficiency by comparing metal concentration before and after passing the organic liquid through the coated porous membrane.

Example 1

This example demonstrates the preparation of surface modification solution which includes monomers with negative charges as well as a radical initiator i.e. materials to form coating.

In a representative experiment, a solution was made which includes: 0.4% Irgacur 2959; 6% Methanol, 5% Vinyl sulfonic acid salt (N-SVN-25); 2% Dimethyl acrylamide (DMAm), 2% Acrylamido methyl Propane sulfonic acid (AMPS), 2% methylene bis acrylamide (MBAm) cross linker, 82.6% water.

Example 2

This example demonstrates the preparation of surface modification solution containing monomers with positive charges, as well as a radical initiator i.e. materials to form coating.

In a representative experiment, a solution was made containing: 0.3% Irgacure 2959, 3.5% Methanol 5.6% Acrylamido propyl trimethylammonium Chloride (APTAC), 1.2% Dimethyl acrylamide (DMAm) and 1.2% methylene bis acrylamide (MBAm) cross linker, 88.2% water.

Example 3

This example demonstrates how a polyethylene membrane is surface modified with a coating having polymerized monomer with negative charges.

In a representative experiment, 47 mm disk of UPE porous membrane (9 psi average mean bubble point in IPA, Entegris, Inc.) was wet with IPA solution for 25 sec. An exchange solution comprising 10% hexylene glycol and 90% water was used to rinse the membrane and remove IPA. The porous membrane disk was then introduced into the surface modification solutions described in Example 1. The dish was covered and the porous membrane was soaked in the solution for 2 minutes. The porous membrane disk was removed and placed between 1 mil polyethylene sheets. The excess solution was removed by rolling a rubber roller over the polyethylene/membrane disk/polyethylene sandwich as it lays flat on a table. The polyethylene sandwich was then taped to a transport unit which conveyed the assembly through a Fusion Systems broadband UV exposure lab unit emitting at wavelengths from 200 to 600 nm. Time of exposure was controlled by how fast the assembly moves through the UV unit. In this example, the assembly moved through the UV chamber at 10 feet per minute. After emerging from the UV unit, the membrane was removed from the sandwich and immediately placed in DI water, where it was washed by swirling for 5 minutes. Next, the treated membrane sample was washed in methanol for 5 minutes. Following this washing procedure the membrane was dried on a holder in an oven operating at 50° C. for 10 min. IPA flow time of the membrane modified as described above was 135 sec.

Example 4

This example demonstrates how a polyethylene membrane is surface modified to with coating having polymerized monomer with positive charge.

In a representative experiment, 47 mm disk of UPE membrane (9 psi average mean bubble point in IPA, Entegris, Inc.) was wet with IPA solution for 25 sec. An exchange solution comprising 10% hexylene glycol and 90% water was used to rinse the membrane and remove IPA. The membrane disk was then introduced into the surface modification solution described in Example 2. The dish was covered and the membrane was soaked in the solution for 2 minutes. The membrane disk was removed and placed between 1 mil polyethylene sheets. The excess solution was removed by rolling a rubber roller over the polyethylene/membrane disk/polyethylene sandwich as it lays flat on a table. The polyethylene sandwich was then taped to a transport unit which conveyed the assembly through a Fusion Systems broadband UV exposure lab unit emitting at wavelengths from 200 to 600 nm. Time of exposure was controlled by how fast the assembly moves through the UV unit. In this example, the assembly moved through the UV chamber at 10 feet per minute. After emerging from the UV unit, the membrane was removed from the sandwich and immediately placed in DI water; where the membrane was washed by swirling for 5 minutes. Next, the treated membrane sample was washed in methanol for 5 minutes. Following this washing procedure the membrane was dried on a holder in an oven operating at 50° C. for 10 min. The IPA flow time of the membrane modified as described above was 240 sec.

Example 5

This example illustrates how the dye binding capacity of the membrane modified according to Example 3 was determined.

Figure 2:
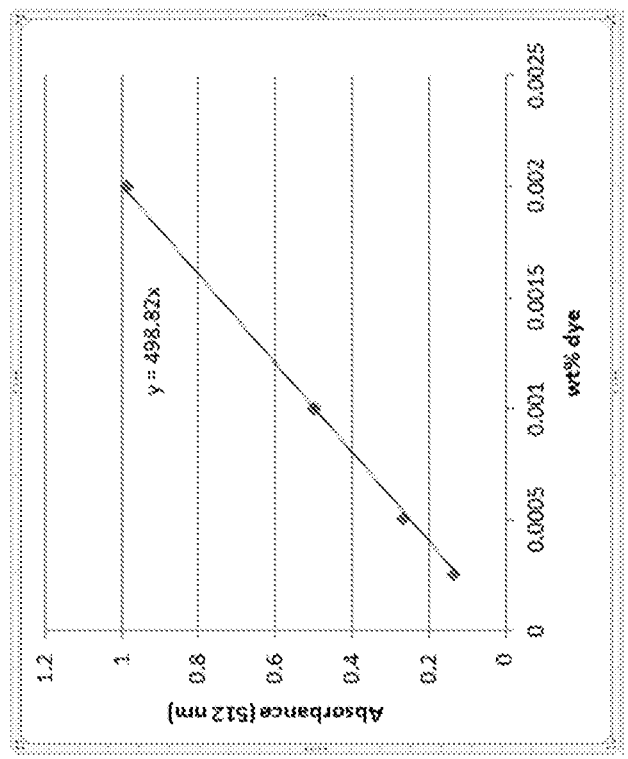
FIG. 2 is a calibration curve of dye solution absorbance data by weight % of mass of dye bound per membrane unit area in accordance with an embodiment of the disclosure.

To confirm that the process of Example 3 resulted in a negatively charged UPE membrane the following experiment was carried out: The dry 47 mm disk membrane of Example 3 was placed in a beaker containing 0.00075 weight % Methylene blue dye (Sigma). The beaker was covered and the membrane was soaked for 5 minutes with continuous mixing at room temperature. The membrane disk was then removed and the absorbance of the dye solution was measured using a Cary spectrophotometer (Agilent Technologies) operating at 666 nm and compared to the absorbance of starting solution (before membrane soaking). Since the dye is cationic in nature it bound to the negatively charged membrane with an average dye binding capacity measured in micrograms (μg) per centimeter squared of 22 μg/cm$^2$. The calibration curve depicted in FIG. 2 was used to convert dye solution absorbance data to weight % and finally mass of dye bound per membrane unit area.

The absorbance of 3 dye solutions with known concentrations was determined using a Cary Spectrophotometer at 666 nm wavelength and used to obtain a calibration curve. The slope of the curve was used to convert the absorbance of the dye solution before and after soaking the membrane to weight % and finally mass of dye bound per membrane unit area.

Example 6

This example illustrates how the dye binding capacity of the membrane modified according to Example 4 was determined.

Figure 3:
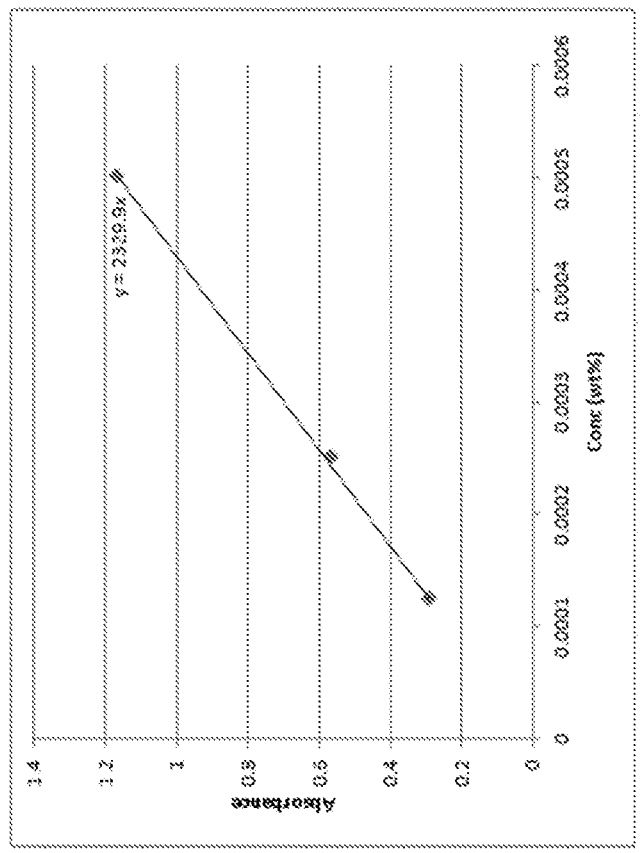
FIG. 3 is another calibration curve of dye solution absorbance data by weight % of mass of dye bound per membrane unit area in accordance with an embodiment of the disclosure.

To confirm that the process of Example 4 resulted in a positively charged UPE membrane the following experiment was carried out: The dry 47 mm disk membrane of Example 4 was placed in a beaker containing 0.002 weight % Ponceau-S dye (Sigma). The beaker was covered and the membrane was soaked for 5 minutes with continuous mixing at room temperature. The membrane disk was then removed and the absorbance of the dye solution was measured using a Cary spectrophotometer (Agilent Technologies) operating at 512 nm and compared to the absorbance of starting solution (before membrane soaking). Because the dye is anionic in nature, the dye is bound to the positively charged membrane with an average dye binding capacity measured in micrograms (μg) per centimeter squared of 54 μg/cm$^2$. The calibration curve depicted in FIG. 3 was used to convert dye solution absorbance data to weight % and finally mass of dye bound per membrane unit area.

The absorbance of 4 dye solutions with known concentrations was determined using a Cary Spectrophotometer at 512 nm wavelength and used to obtain a calibration curve. The slope of the curve was used to convert the absorbance of the dye solution before and after soaking the membrane to weight % and finally mass of dye bound per membrane unit area.

Example 7

This example illustrates the metal removal efficiency in cyclohexanone of a device comprising membrane prepared as described in Example 3.

A device was made comprising 1000 cm$^2$ of the membrane prepared according to Example 3. The device was connected to a testing line and challenged with cyclohexanone feed solution as described in the general metal removal test procedure section. A challenge solution was prepared by spiking 1 ml of CONOSTAN S-12 Standard (SCP science, oil based 12 metal standard, 10 ppm total concentration) into 1 L of cyclohexanone solution (Sigma). Resulting metal concentration in the challenge solution was determined using ICP-MS and is depicted in Table 1. The concentration of metals decreased significantly, after filtration through the positively charged membrane device. Removal efficiency ranged from 73.7 to 99.8% depending on metal type.

TABLE 1

| Metal | Feed metal concentration (ppb) | Filtrate metal concentration (ppb) | % Removal (1200 ml) |
|---|---|---|---|
| Na | 144.6 | 7.4 | 94.9 |
| Mg | 4.2 | 0.01 | 99.8 |
| Al | 4.1 | 0.2 | 95 |
| Fe | 9.4 | 0.5 | 94.7 |
| Ti | 5.2 | 0.1 | 98.1 |
| Cr | 5.7 | 1.5 | 73.7 |
| Ni | 5.4 | 0.3 | 94 |
| Cu | 6.8 | 0.4 | 94 |
| Zn | 3.3 | 0.1 | 96.9 |
| Ag | 5.4 | 0.3 | 94 |
| Sn | 6.4 | 0.2 | 97 |
| Pb | 5.0 | 0.1 | 98 |
| Total metals | 205.5 | 11.11 | 95 |

Example 8

This example illustrates the metal removal efficiency in Cyclohexanone of a device comprising membrane prepared as described in Example 4.

A device was made comprising 1000 cm$^2$ of the membrane prepared according to Example 4. The device was connected to a testing line and challenged with cyclohexanone feed solution as described in the general metal removal test procedure section. A challenge solution was prepared by spiking 0.5 ml of CONOSTAN S-12 Standard (SCP science, oil based 12 metal standard, 10 ppm total concentration) into 1 L of cyclohexanone solution (Sigma). Resulting metal concentration in the challenge solution was determined using ICP-MS and is depicted in Table 2. The concentration of metals decreased after filtration through the negatively charged membrane device. Removal efficiency ranged from 17.9 to 99.2% depending on metal type.

TABLE 2

| Metal | Feed metal concentration (ppb) | Filtrate metal concentration (ppb) | % Removal (1200 ml) |
|---|---|---|---|
| Na | 42 | 0.32 | 99.2 |
| Mg | 3.6 | 0.29 | 91.9 |
| Al | 3.7 | 0.96 | 74.2 |
| Ti | 4.1 | 0.48 | 88.2 |
| Cr | 4.6 | 3.37 | 26.8 |
| Fe | 5.9 | 2.12 | 64.0 |
| Ni | 4.2 | 1.72 | 59.1 |
| Cu | 4.6 | 1.19 | 73.9 |
| Ag | 4 | 3.28 | 17.9 |
| Sn | 5.34 | 1.59 | 69.9 |
| Pb | 3.5 | 0.29 | 91.8 |
| Total metals | 47.74 | 15.6 | 67.32 |

Example 9

This example illustrates the improved metal removal efficiency in cyclohexanone when an embodiment of a device with a positively charged membrane is used instead of a device with a negatively charged membrane. Common metals present in cyclohexanone solution according to Example 7 and Example 8, were plotted in FIG. 5 to demonstrate the surprising superior metal removal efficiency of positively charged membrane device (black bars) e.g. 510 in comparison to negatively charged membrane device (gray bars) e.g. 520 for the elements Na, Mg, Al, Fe, Ti, Cr, Ni, Cu, Ag, Sn, and Pb.

Figure 5:
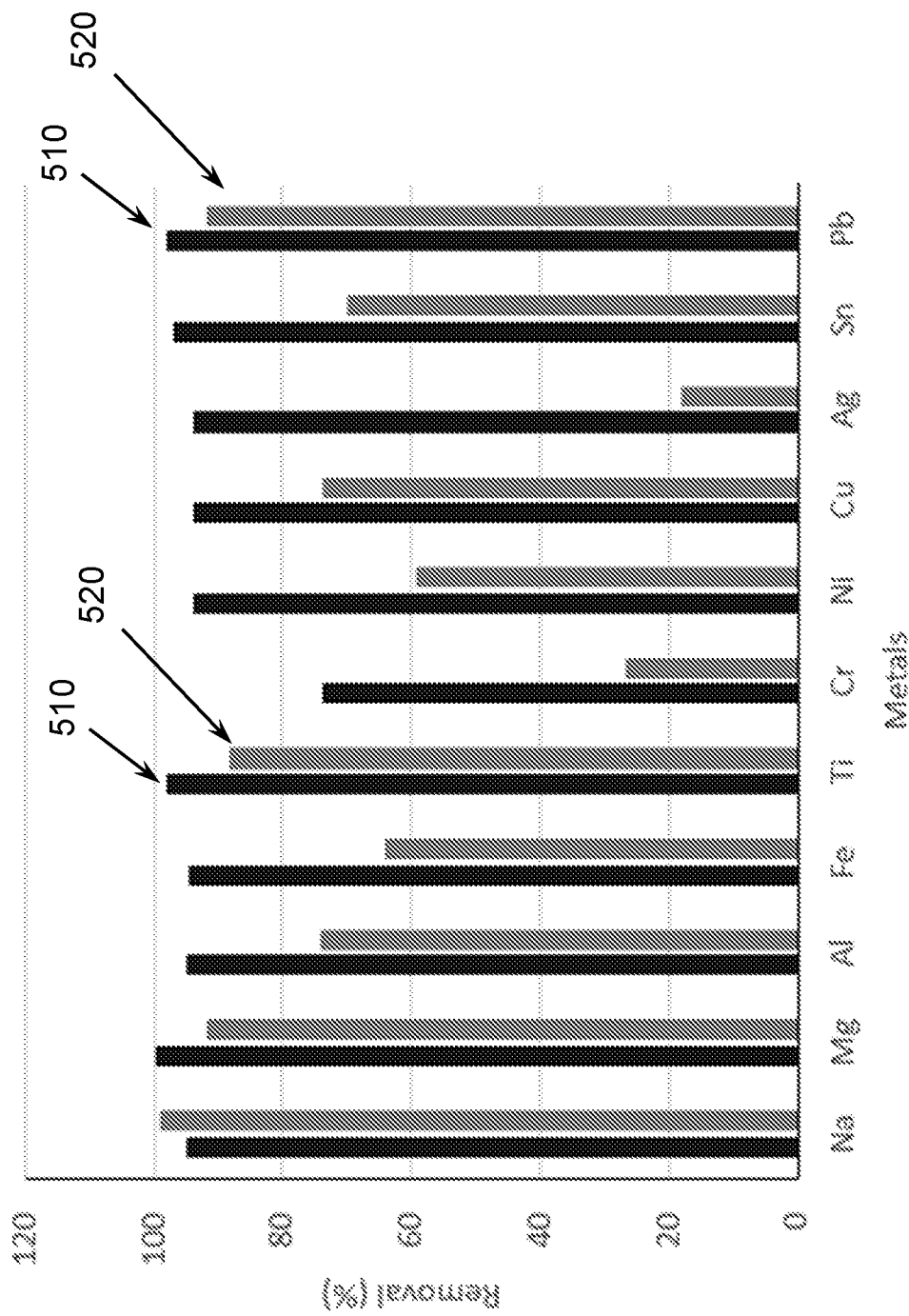
FIG. 5 is a comparative graph of removing metal contaminants from cyclohexanone with membranes in a device in accordance with an embodiment of the disclosure.

FIG. 5 is a comparative graph of removing metal contaminants from cyclohexanone with an embodiment of positively charged membrane device 200 vs. a negatively charged membrane device and comparatively shows the difference in removing metal contaminants from liquids that are miscible with and not miscible with water. FIG. 5 demonstrates the method, membrane and device unexpectedly and efficiently remove metal contaminants from water immiscible organic liquid by at least 95% after passing the water immiscible organic liquid thru the porous membrane.

Example 10

Charge density determination of negatively Charged 0.65 micron (μm) bubble point pore size rated UPE Membrane prepared as described in Example 3

Six 47 mm diameter membrane coupons were cut from a cross section of a negatively charged 0.65 μm UPE membrane. The membranes were prewet with IPA and exchanged into water. The wetted membrane were conditioned by dipping into 1.0 N HCl followed by submerging in 100 mL of 0.1 N HCl for 5 minutes with stirring. The HCl conditioned membrane were repeatedly washed in fresh 200 mL deionized water until the pH of the deionized water wash stabilized at pH of +/−1 relative to the fresh (not exposed to membrane) deionized water reading. The membranes were then placed in 100 mL of 1 M NaCl and stirred for 2 minutes and the membranes were removed and discarded. The 100 mL of 1 M NaCl that was exposed to the membrane had a pH of 2.76. The solution was titrated with 0.001 M NaOH and the volume of NaOH to reach pH 7.0 was recorded. The charge density of the negatively charged membrane was determined to be 8.08 meq/m$^2$. For comparison, an unmodified 0.65 um UPE membrane was run as a control and the charge density was determined to be 0.05 meq/m$^2$. Although the charge density of the negatively charged membrane was determined to be 8.08 meq/m$^2$, the charge density of the negatively charged membrane may range from about 0.5 to about 20 meq/m$^2$. In an embodiment, the negatively charged membrane has a charge density from about 2.0 meq/m$^2$ to 15 meq/m$^2$, 4.0 meq/m$^2$ to 15 meq/m$^2$, 5 meq/m$^2$ to 13 meq/m$^2$, 6 meq/m$^2$ to 12 meq/m$^2$, and 7.0 meq/m$^2$ to 9 meq/m$^2$.

Example 11

Charge density determination of positively Charged 0.65 μm UPE Membrane prepared as described in Example 4. Six 47 mm diameter membrane coupons were cut from a cross section of a positively charged 0.65 μm rated UPE membrane. The membranes were prewet with IPA and exchanged into water. The wetted membrane were conditioned by dipping into 1.0 N NaOH followed by submerging in 100 mL of 0.1 N NaOH for 5 minutes with stirring. The NaOH conditioned membrane were repeatedly washed in fresh 200 mL deionized water until the pH of the deionized water wash stabilized at pH of +/−1 relative to the fresh (not exposed to membrane) deionized water reading. The membranes were then placed in 100 mL of 1 M NaCl and stirred for 2 minutes and the membranes were removed and discarded. The 100 mL of 1 M NaCl that was exposed to the membrane had a pH of 10.01. The solution was titrated with 0.001 M HCl and the volume of HCl to reach pH 7.0 was recorded. The charge density of the positively charged membrane was determined to be 2.31 meq/m2. An unmodified 0.65 um UPE membrane was run as a control and the charge density was determined to be 0.00 meq/m2. Although the charge density of the positively charged membrane was determined to be 2.31 meq/m$^2$, the charge density of the positively charged membrane may range from about 0.5 meq/m$^2$ to about 20 meq/m$^2$. In an embodiment, the positively charged membrane has a charge density from about 2.0 meq/m$^2$ to 15 meq/m$^2$, 4.0 meq/m$^2$ to 15 meq/m$^2$, 5 meq/m$^2$ to 13 meq/m$^2$, 6 meq/m$^2$ to 12 meq/m$^2$, 7.0 meq/m$^2$ to 9 meq/m$^2$, 5.0 meq/m$^2$ to 7 meq/m$^2$, and 4.0 meq/m$^2$ to 6 meq/m$^2$.

Thus, embodiments of the disclosure include membranes with specific charge density and method of making such membranes with a given charge density. The charge density is not limited to the particular value such as 2.31 meq/m$^2$, 2.25 meq/m$^2$, 2.20 meq/m$^2$, but for illustration and not limitation of making positively charged membranes with charge density.

Example 12

Solvent Filtration Experiments: Single Layer Membrane

Figure 6:
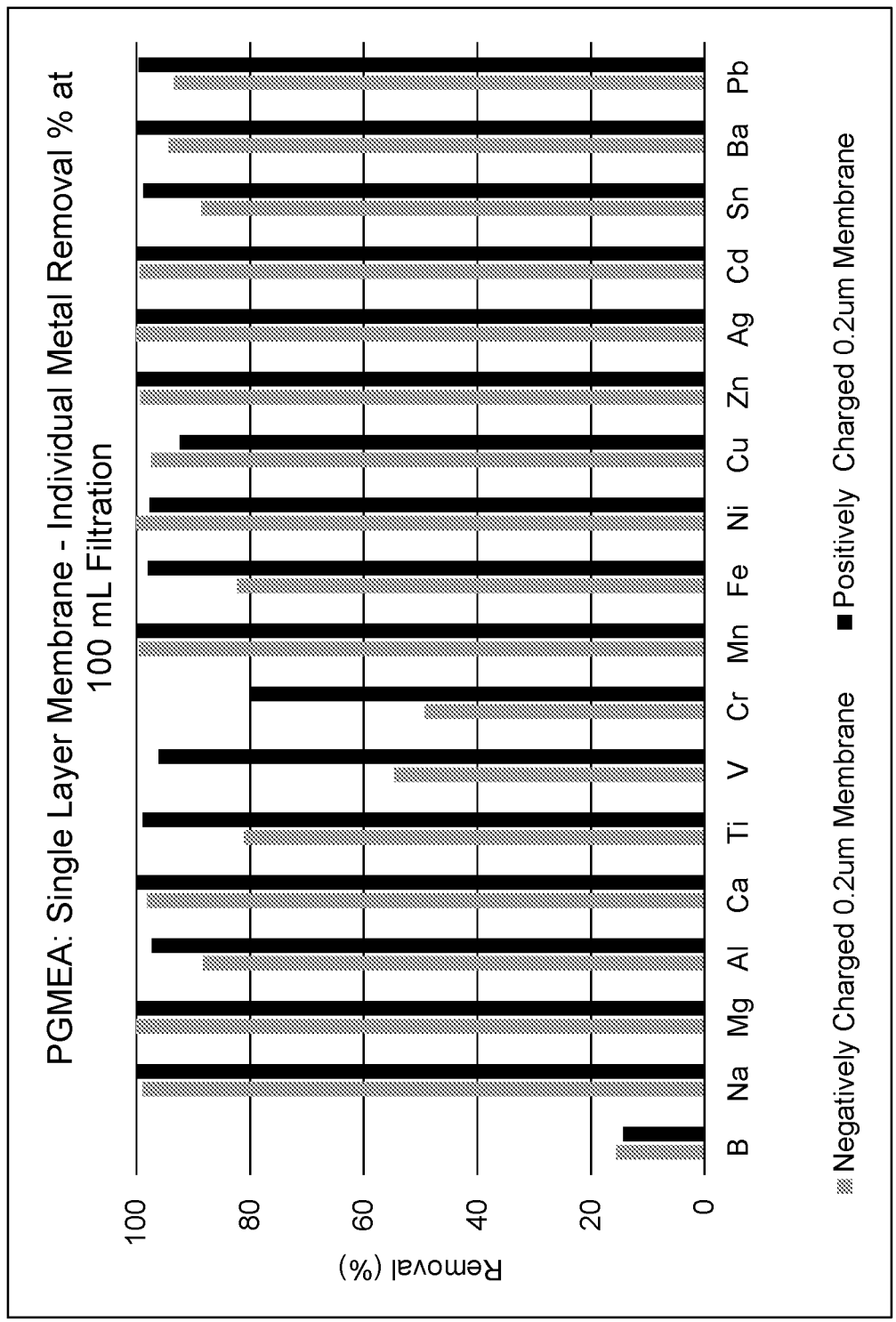
FIG. 6 is a comparative graph of removing metal contaminants from PGMEA organic liquid showing removal by a single layer porous polymeric membrane with a cross-linked coating comprising a polymerized monomer that is positively charged in the organic liquid compared with removal by a single layer porous polymeric membrane with a cross-linked coating comprising a polymerized monomer that is negatively charged in the organic liquid.
Figure 7:
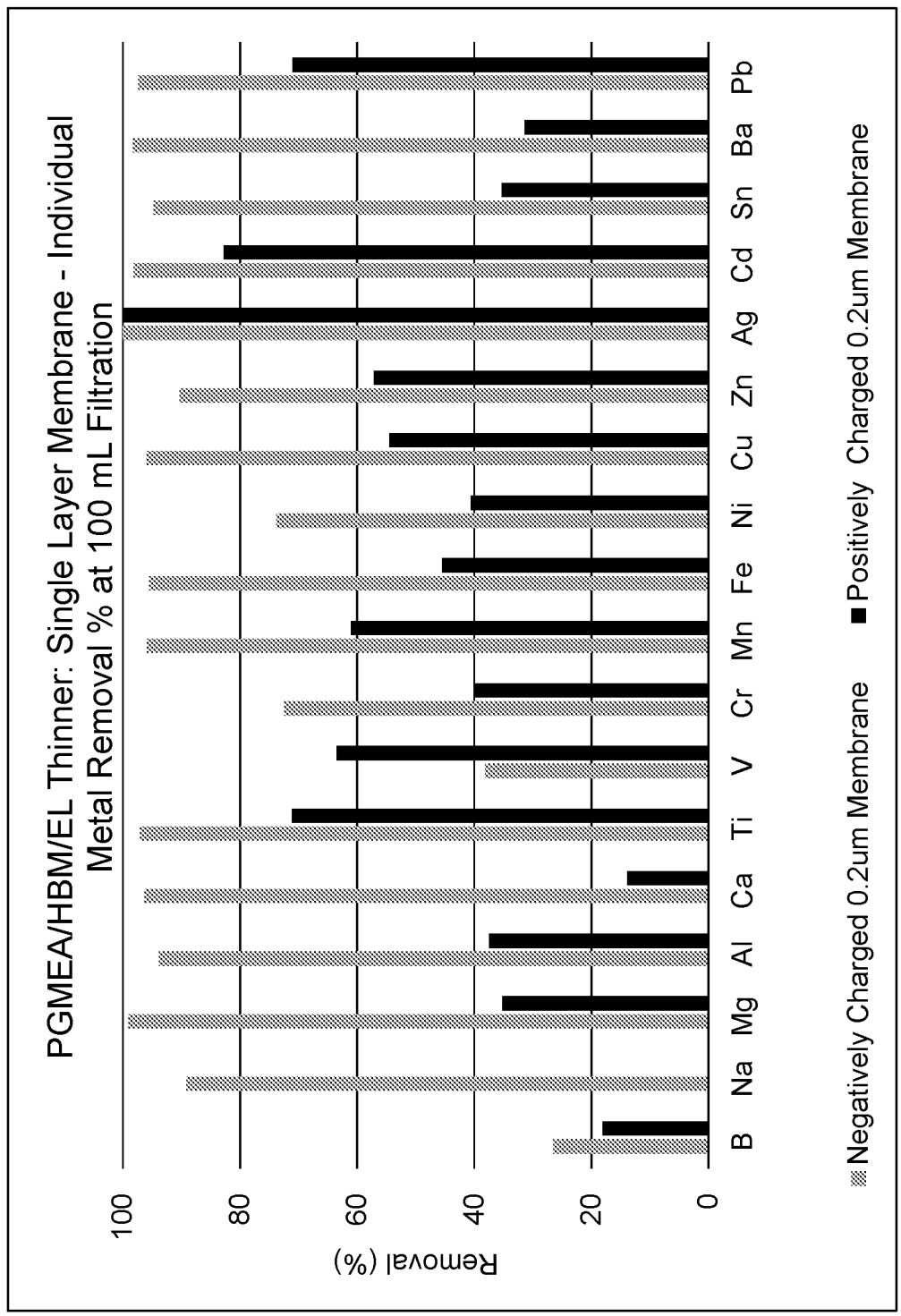
FIG. 7 is a comparative graph of removing metal contaminants PGMEA/HBM/EL thinner showing removal by a single layer porous polymeric membrane with a cross-linked coating comprising a polymerized monomer that is positively charged in the organic liquid compared with removal by a single layer porous polymeric membrane with a cross-linked coating comprising a polymerized monomer that is negatively charged in the organic liquid.
Figure 8:
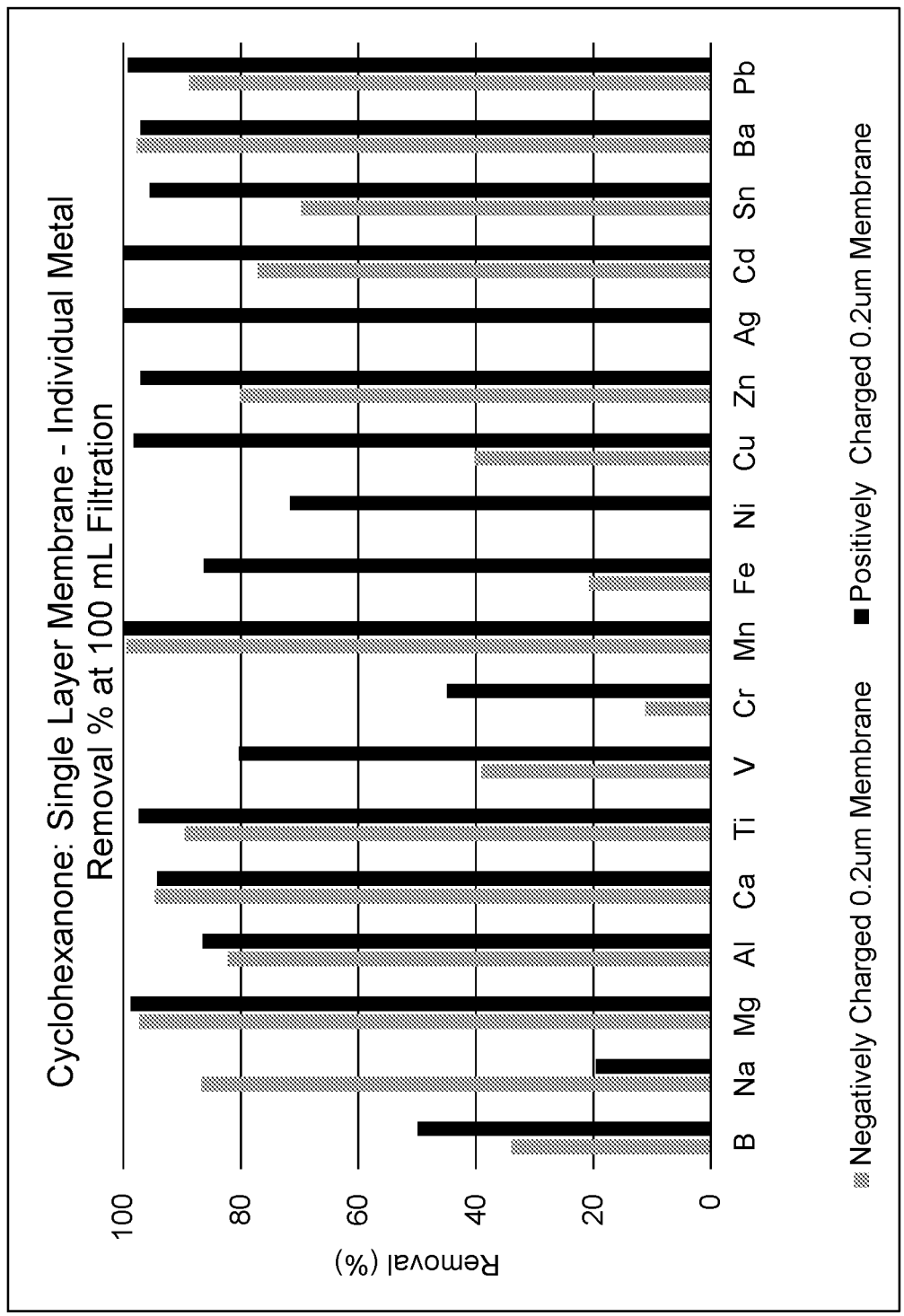
FIG. 8 is a comparative graph of removing metal contaminants from Cyclohexanone organic liquid showing removal by a single layer porous polymeric membrane with a cross-linked coating comprising a polymerized monomer that is positively charged in the organic liquid compared with removal by a single layer porous polymeric membrane with a cross-linked coating comprising a polymerized monomer that is negatively charged in the organic liquid.
Figure 9:
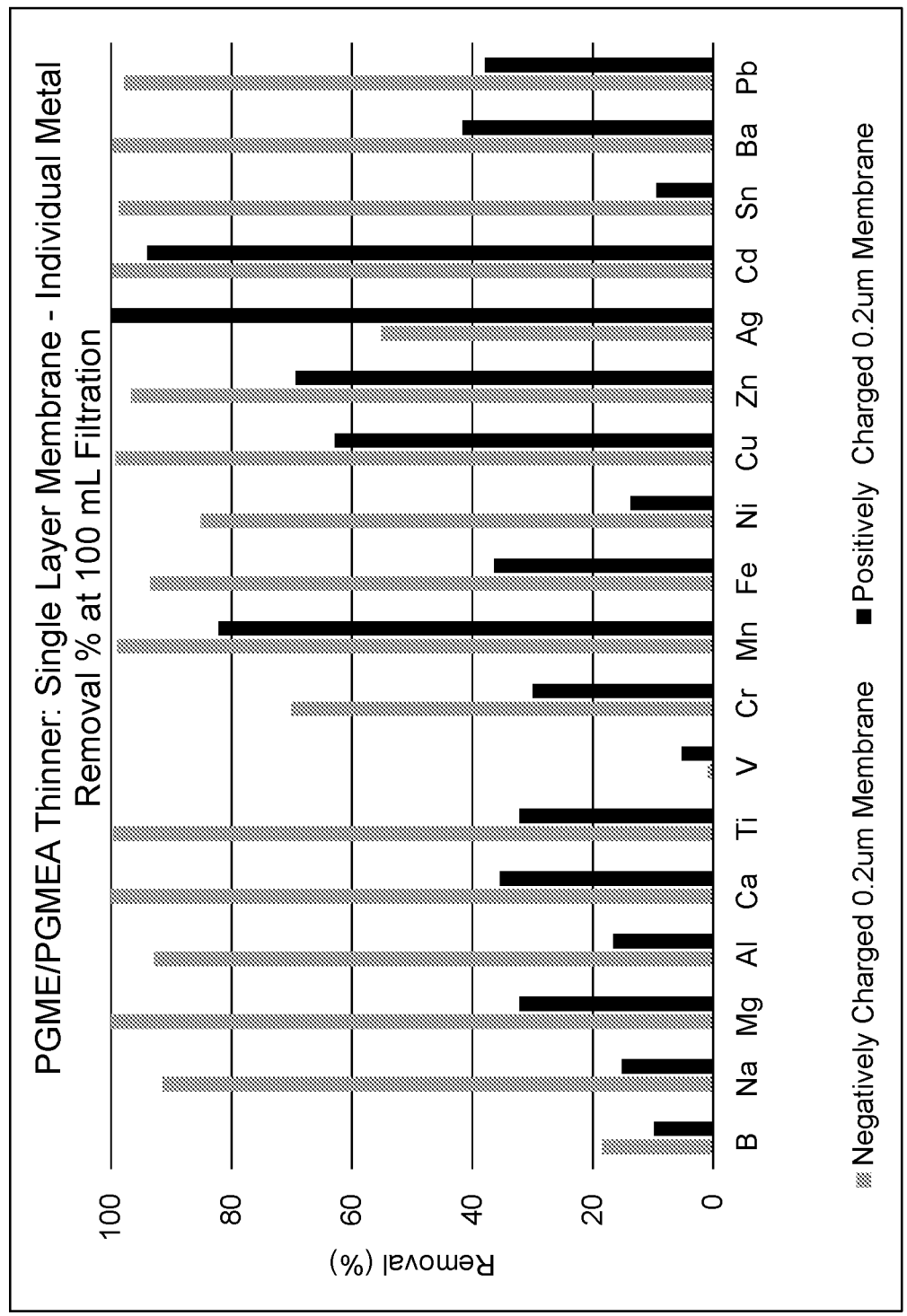
FIG. 9 is a comparative graph of removing metal contaminants from PGMEA/PGME thinner organic liquid showing removal by a single layer porous polymeric membrane with a cross-linked coating comprising a polymerized monomer that is positively charged in the organic liquid compared with removal by a single layer porous polymeric membrane with a cross-linked coating comprising a polymerized monomer that is negatively charged in the organic liquid.
Figure 10:
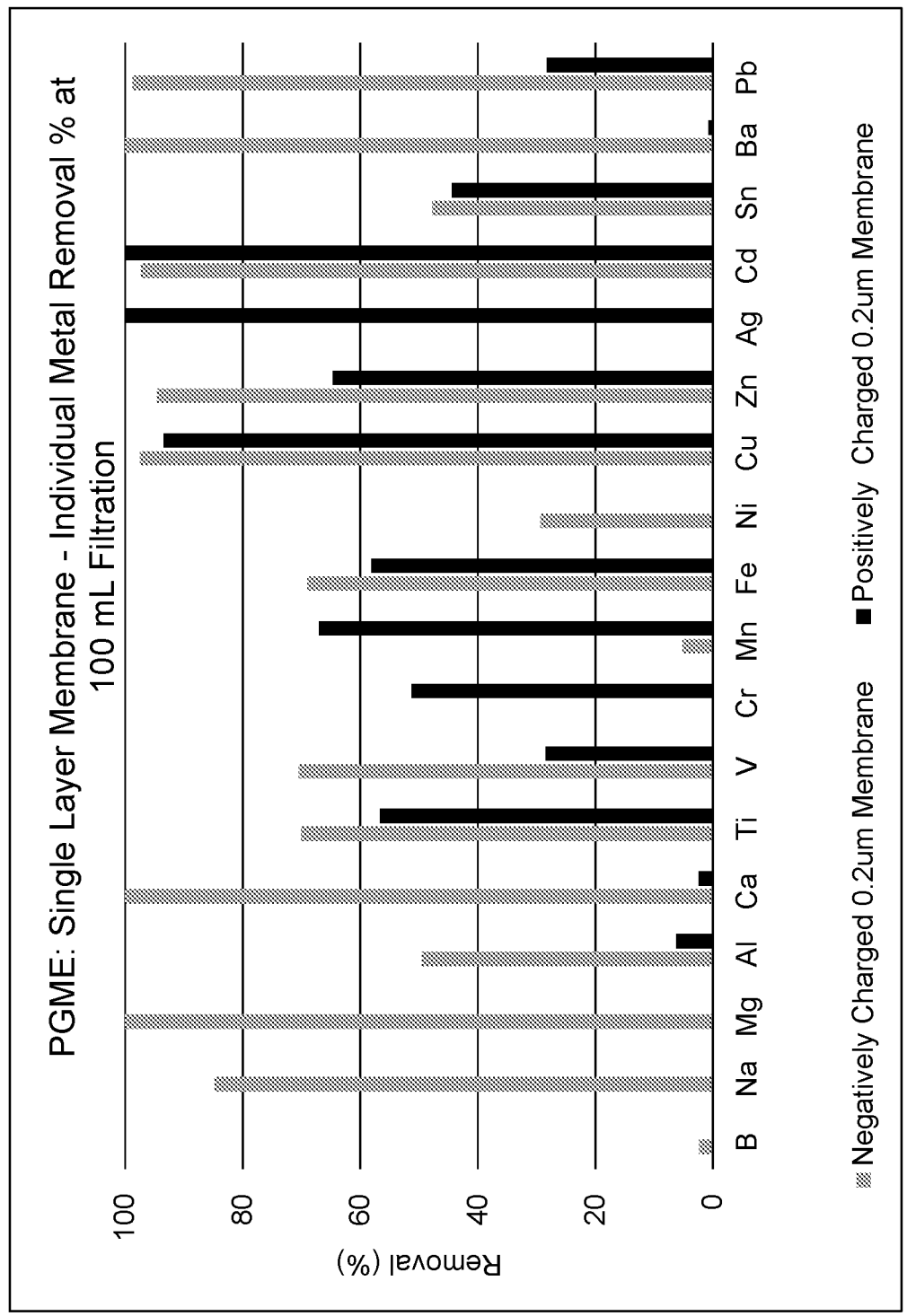
FIG. 10 is a comparative graph of removing metal contaminants from PGME organic liquid showing removal by a single layer porous polymeric membrane with a cross-linked coating comprising a polymerized monomer that is positively charged in the organic liquid compared with removal by a single layer porous polymeric membrane with a cross-linked coating comprising a polymerized monomer that is negatively charged in the organic liquid.

Positively and Negatively charged 0.2 μm UPE membranes were prepared using a method similar to Example 3 and Example 4 and cut into 47 mm membrane coupons. These membrane coupons were conditioned by washing several times with 10% HCl followed by soaking in 10% HCl overnight and equilibrated with deionized water. For each sample, one 47 mm membrane coupon was secured into a clean PFA 47 mm Single Stage Filter Assembly (Savillex). The membrane and filter assembly were flushed with IPA followed by application solvent. The application solvents include Cyclohexanone, a PGME (propylene glycol monomethyl ether) composition, a PGME/PGMEA thinner, PGMEA (propylene glycol monomethyl ether acetate), and a PGMEA/HBM (methyl 2-hydroxy-2-methyl propionate)/EL (ethyl lactate) mixture. The application solvents were spiked with CONOSTAN Oil Analysis Standard S-21 (SCP Science) at a target concentration of 5 ppb of each metal. To determine the filtration metal removal efficiency the metal spiked application solvents were passed through the corresponding 47 mm filter assembly containing each filter at 10 mL/min and the filtrate was collected into a clean PFA jar at 50 mL, 100 mL, and 150 mL. The metal concentration for the metal spiked application solvent and each filtrate sample was determined using ICP-MS. The results are depicted in Total Metals Removal (%) in Table 3 and Individual Metal Removal Nat 100 mL Filtration in FIG. 6 (PGMEA), FIG. 7 (PGMEA/HBM/EL), FIG. 8 (Cyclohexanone), FIG. 9 (PGME/PGMEA thinner), and FIG. 10 (PGME).

TABLE 3

| | 0.2 um Membrane | | | | | |
|---|---|---|---|---|---|---|
| | Negatively Charged | | | Positively Charged | | |
| Application Solvent | | | | | | |
| | PGMEA | | | | | |
| Filtration Volume (mL) | 50 | 100 | 150 | 50 | 100 | 150 |
| Total Metals Removal (%) | 88.7 | 87.4 | 87.0 | 93.4 | 93.6 | 93.4 |

TABLE 3-continued

| | 0.2 um Membrane | | | | | |
|---|---|---|---|---|---|---|
| Application Solvent | Negatively Charged | | | Positively Charged | | |
| | PGMEA/HBM/EL | | | | | |
| Filtration Volume (mL) | 50 | 100 | 150 | 50 | 100 | 150 |
| Total Metals Removal (%) | 88.1 | 85.6 | 86.0 | 59.5 | 44.4 | 42.8 |
| | (Cyclohexanone) | | | | | |
| Filtration Volume (mL) | 50 | 100 | 150 | 50 | 100 | 150 |
| Total Metals Removal (%) | 77.2 | 74.0 | 73.2 | 89.2 | 90.4 | 89.6 |
| | PGME/PGMEA Thinner | | | | | |
| Filtration Volume (mL) | 50 | 100 | 150 | 50 | 100 | 150 |
| Total Metals Removal (%) | 88.4 | 87.7 | 82.1 | 49.9 | 36.9 | 33.8 |
| | PGME | | | | | |
| Filtration Volume (mL) | 50 | 100 | 150 | 50 | 100 | 150 |
| Total Metals Removal (%) | 71.2 | 66.0 | 65.4 | 47.3 | 36.4 | 34.6 |

Example 13

Solvent Filtration Experiments: Two Layer Membrane

Figure 11:
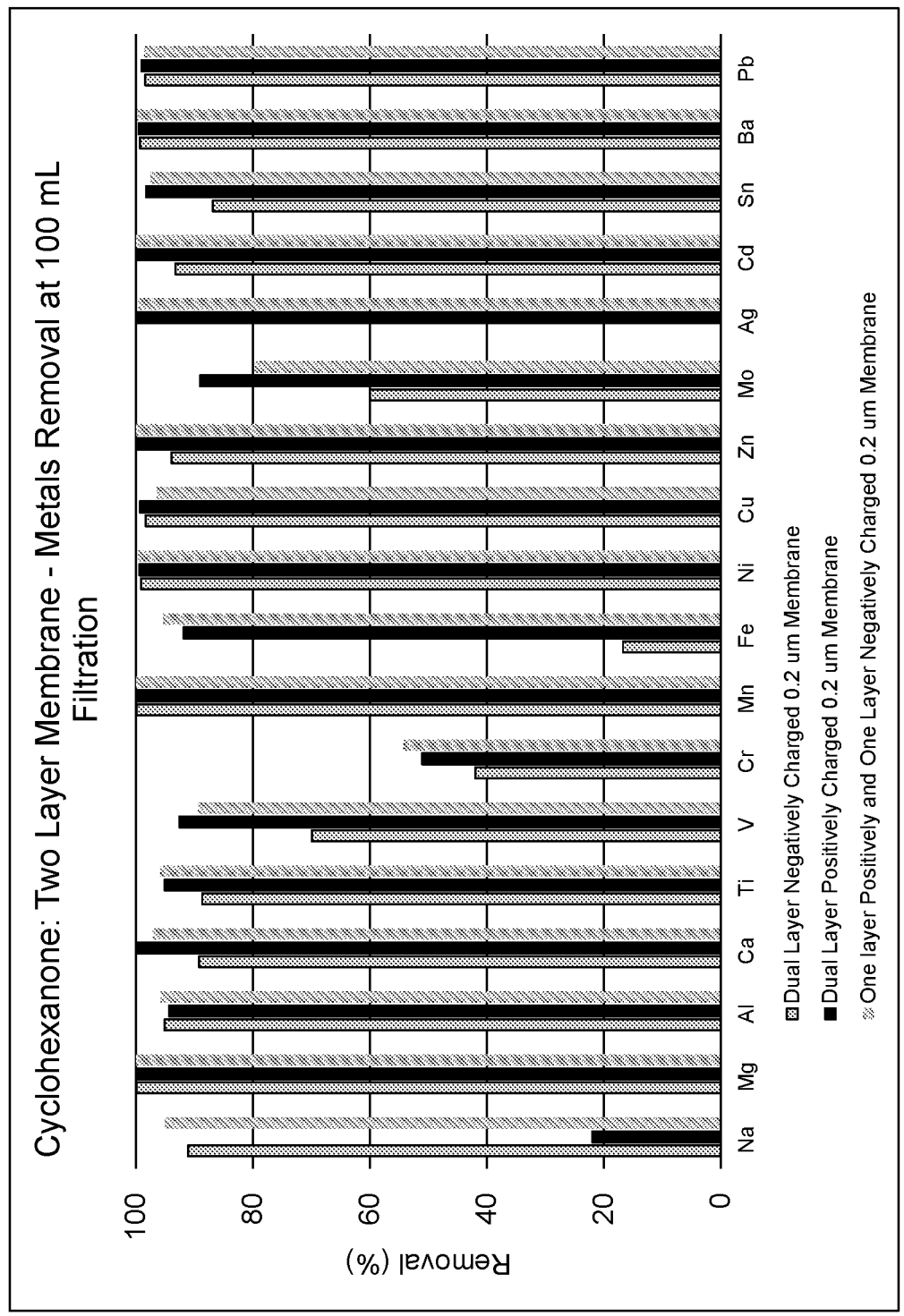
FIG. 11 is a comparative graph of removing metal contaminants from cyclohexanone organic liquid showing metals removal by: a two porous polymeric membranes each with a cross-linked coating comprising a polymerized monomer that is positively charged in the organic liquid; two porous polymeric membranes each with a cross-linked coating comprising a polymerized monomer that is negatively charged in the organic liquid; and two porous membranes, one with a cross-linked coating comprising a monomer that is positively charged in the organic liquid and one with a cross-linked coating comprising a monomer that is negatively charged in the organic liquid.
Figure 12:
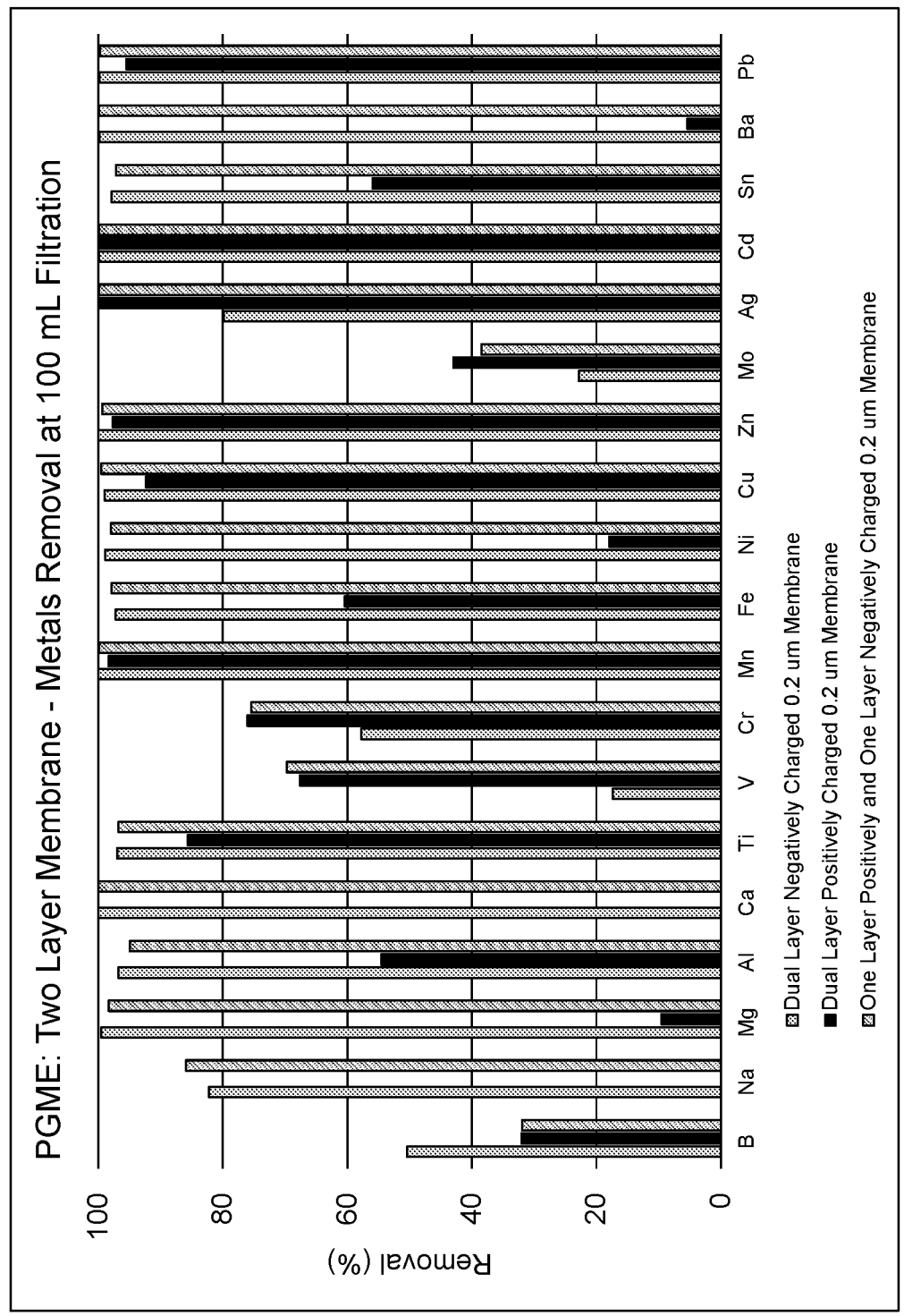
FIG. 12 is a comparative graph of removing metal contaminants from PGME organic liquid showing metals removal by: a two porous polymeric membranes each with a cross-linked coating comprising a polymerized monomer that is positively charged in the organic liquid; two porous polymeric membranes each with a cross-linked coating comprising a polymerized monomer that is negatively charged in the organic liquid; and two porous membranes, one with a cross-linked coating comprising a monomer that is positively charged in the organic liquid and one with a cross-linked coating comprising a monomer that is negatively charged in the organic liquid.

This example demonstrates the ability for two layer format coated membrane materials to reduce metals in solvents. Positively and Negatively charged 0.2 μm UPE membranes were prepared using a method similar to Example 3 and Example 4 and cut into 47 mm membrane coupons. These membrane coupons were conditioned by washing several times with 10% HCl followed by soaking in 10% HCl overnight and equilibrated with deionized water. For each sample, two 47 mm membrane coupons were layered on top of each other and secured into a clean 47 mm Filter Assembly (Savillex) resulting in a two layer filter. The membrane and filter assembly were flushed with IPA followed by application solvent. The application solvents include Cyclohexanone, and PGME thinner. The application solvents were spiked with CONOSTAN Oil Analysis Standard S-21 (SCP Science) at a target concentration of 5 ppb of each metal. To determine the filtration metal removal efficiency the metal spiked application solvents were passed through the corresponding 47 mm dual layer filter assembly containing each filter at 10 mL/min and the filtrate was collected into a clean PFA jar at 50 mL, 100 mL, and 150 mL. The metal concentration for the metal spiked application solvent and each filtrate sample was determined using ICP-MS. The results are depicted in Total Metals Removal (%) in Table 4 and Individual Metal Removal % at 100 mL Filtration in FIG. 11 (cyclohexanone), and FIG. 12 (PGME).

TABLE 4

| | 0.2 um Membrane | | | | | | | | |
|---|---|---|---|---|---|---|---|---|---|
| Application Solvent | Two Negatively Charged Layers | | | Two Positively Charged Layers | | | One Layer of Positive Charge and One Layer of Negative Charge | | |
| | (Cyclohexanone) | | | | | | | | |
| Filtration Volume (mL) | 50 | 100 | 150 | 50 | 100 | 150 | 50 | 100 | 150 |
| Total Metals Removal (%) | 86.0 | 84.9 | 84.3 | 97.4 | 94.2 | 93.0 | 97.2 | 96.4 | 95.9 |
| | PGME | | | | | | | | |
| Filtration Volume (mL) | 50 | 100 | 150 | 50 | 100 | 150 | 50 | 100 | 150 |
| Total Metals Removal (%) | 83.7 | 86.1 | 85.6 | 61.0 | 56.7 | 55.1 | 93.0 | 90.9 | 88.1 |

Example 14

Solvent Static Soaking Experiments

This example demonstrates the ability for coated membrane materials to reduce metals in solvents under static soaking conditions. Positively and Negatively charged 0.2 µm UPE membranes were prepared using a method similar to Example 3 and Example 4 and cut into 47 mm membrane coupons. These membrane coupons were conditioned by washing several times with 10% HCl followed by soaking in 10% HCl overnight, equilibrated with deionized water, and allowed to dry at room temperature. The application solvents include Cyclohexanone, PGME, PGME/PGMEA THINNER, PGMEA, and a PGMEA/HBM/EL THINNER. The application solvents were spiked with CONOSTAN Oil Analysis Standard S-21 (SCP Science) at a target concentration of 5 ppb of each metal. To determine the static soak metal removal efficiency 25 mL of the metal spiked application solvents were placed in a PFA jar with the conditioned and dried 47 mm membrane coupons. The PFA jar containing the metal spiked application solvents and membrane coupons were rotated for 16 hours. After 16 hours the membrane coupons were removed. The metal concentration for the metal spiked application solvent and each solvent membrane supernatant sample was determined using ICP-MS. The results are provided in % Removal in Table 5.

Acrylamido methyl Propane sulfonic acid (AMPS), 1.76% Acrylamido propyl trimethylammonium Chloride (APTAC), 1.43% methylene bis acrylamide (MBAm) cross linker, 84.87% water.

Example 16

Mixed Charge Membrane Coating

This example demonstrates how a polyethylene membrane is surface modified with coating having polymerized monomers with both positive and negative charges.

In a representative experiment, 47 mm disk of UPE membrane (9 psi average mean bubble point in IPA, Entegris, Inc.) was wet with IPA solution for 25 sec. An exchange solution comprising 10% hexylene glycol and 90% water was used to rinse the membrane and remove IPA. The membrane disk was then introduced into the solution from Example 15. The dish was covered and the membrane was soaked in the solution for 30 seconds. The membrane disk was removed and placed between polyethylene sheets. The excess solution is removed by rolling a rubber roller over the polyethylene/membrane disk/polyethylene sandwich as it lays flat on a table. The polyethylene sandwich was then taped to a transport unit which conveyed the assembly through a Fusion Systems broadband UV exposure lab unit emitting at wavelengths from 200 to 600 nm. Time of

TABLE 5

| | 0.2 µm Membrane | | | | | | | | | |
|---|---|---|---|---|---|---|---|---|---|---|
| | Negatively Charged | Positively Charged | Negatively Charged | Positively Charged | Negatively Charged | Positively Charged | Negatively Charged | Positively Charged | Negatively Charged | Positively Charged |
| Solvent | | | | | | | | | | |
| | PGMEA | | ArF | | CHN | | OK73 | | PGME | |
| Metal | | | | | | | | | | |
| | % Removal | | % Removal | | % Removal | | % Removal | | % Removal | |
| B | 21.3 | 29.0 | 100.0 | 100.0 | 21.9 | 77.1 | 16.4 | 5.1 | 19.0 | 8.7 |
| Na | 92.4 | 99.5 | 92.2 | 75.9 | 95.5 | 50.0 | 96.2 | 0.0 | 82.4 | 0.0 |
| Mg | 100.0 | 100.0 | 100.0 | 100.0 | 99.1 | 99.6 | 100.0 | 85.6 | 100.0 | 6.4 |
| Al | 99.6 | 97.7 | 99.2 | 100.0 | 98.5 | 98.9 | 93.0 | 77.5 | 89.3 | 88.2 |
| Ca | 98.8 | 100.0 | 97.7 | 100.0 | 93.9 | 98.1 | 100.0 | 91.3 | 100.0 | 16.8 |
| Ti | 60.2 | 97.5 | 100.0 | 100.0 | 100.0 | 100.0 | 99.1 | 84.9 | 96.7 | 88.0 |
| V | 95.9 | 98.2 | 100.0 | 100.0 | 94.5 | 97.5 | 0.0 | 77.0 | 97.2 | 59.9 |
| Cr | 86.5 | 98.8 | 100.0 | 100.0 | 63.9 | 77.3 | 82.3 | 51.5 | 5.8 | 71.2 |
| Mn | 99.7 | 100.0 | 100.0 | 100.0 | 99.9 | 100.0 | 99.4 | 93.8 | 39.3 | 85.8 |
| Fe | 94.9 | 100.0 | 97.4 | 99.4 | 72.0 | 100.0 | 95.1 | 87.0 | 97.2 | 89.2 |
| Ni | 96.4 | 99.2 | 100.0 | 100.0 | 95.6 | 97.4 | 85.1 | 86.7 | 98.2 | 16.7 |
| Cu | 97.9 | 98.3 | 100.0 | 100.0 | 99.7 | 97.2 | 100.0 | 93.2 | 100.0 | 96.1 |
| Zn | 97.9 | 98.0 | 99.8 | 98.4 | 98.5 | 100.0 | 96.7 | 94.2 | 98.5 | 89.4 |
| Ag | 0.0 | 17.1 | 100.0 | 100.0 | 0.0 | 75.7 | 0.0 | 81.8 | 32.5 | 93.1 |
| Cd | 97.6 | 99.0 | 100.0 | 100.0 | 99.0 | 100.0 | 97.2 | 99.1 | 99.5 | 98.4 |
| Sn | 94.8 | 97.7 | 100.0 | 100.0 | 92.0 | 99.7 | 57.9 | 63.8 | 64.7 | 84.4 |
| Ba | 99.5 | 100.0 | 99.5 | 100.0 | 99.6 | 98.8 | 97.0 | 89.9 | 99.1 | 29.7 |
| Pb | 94.2 | 99.6 | 100.0 | 100.0 | 100.0 | 100.0 | 99.5 | 86.8 | 99.7 | 93.0 |
| Total Metals | 91.3 | 95.2 | 99.2 | 98.7 | 88.8 | 95.5 | 84.2 | 77.4 | 82.6 | 60.6 |

Example 15

Mixed Charge Coating Solution and Preparation of Mixed Charge Single Layer Membrane This example demonstrates the preparation of surface modification solution which includes individual monomers with positive and negative charges as well as a cross linker and a radical initiator i.e. materials to form coating.

In a representative experiment, a solution was made which includes 0.28% Irgacur 2959; 10% Methanol, 1.66% exposure is controlled by how fast the assembly moves through the UV unit. In this example, the assembly moved through the UV chamber at 12 feet per minute. After emerging from the UV unit, the membrane was removed from the sandwich and immediately placed in DI water, where it was washed by swirling for 5 minutes. Next, the treated membrane sample was washed in methanol for 5 minutes. Following this washing procedure the membrane was dried on a holder in an oven operating at 50° C. for 10 min.

Example 17

Solvent Filtration Experiments: Mixed Charge Single Layer Membrane

Figure 13:
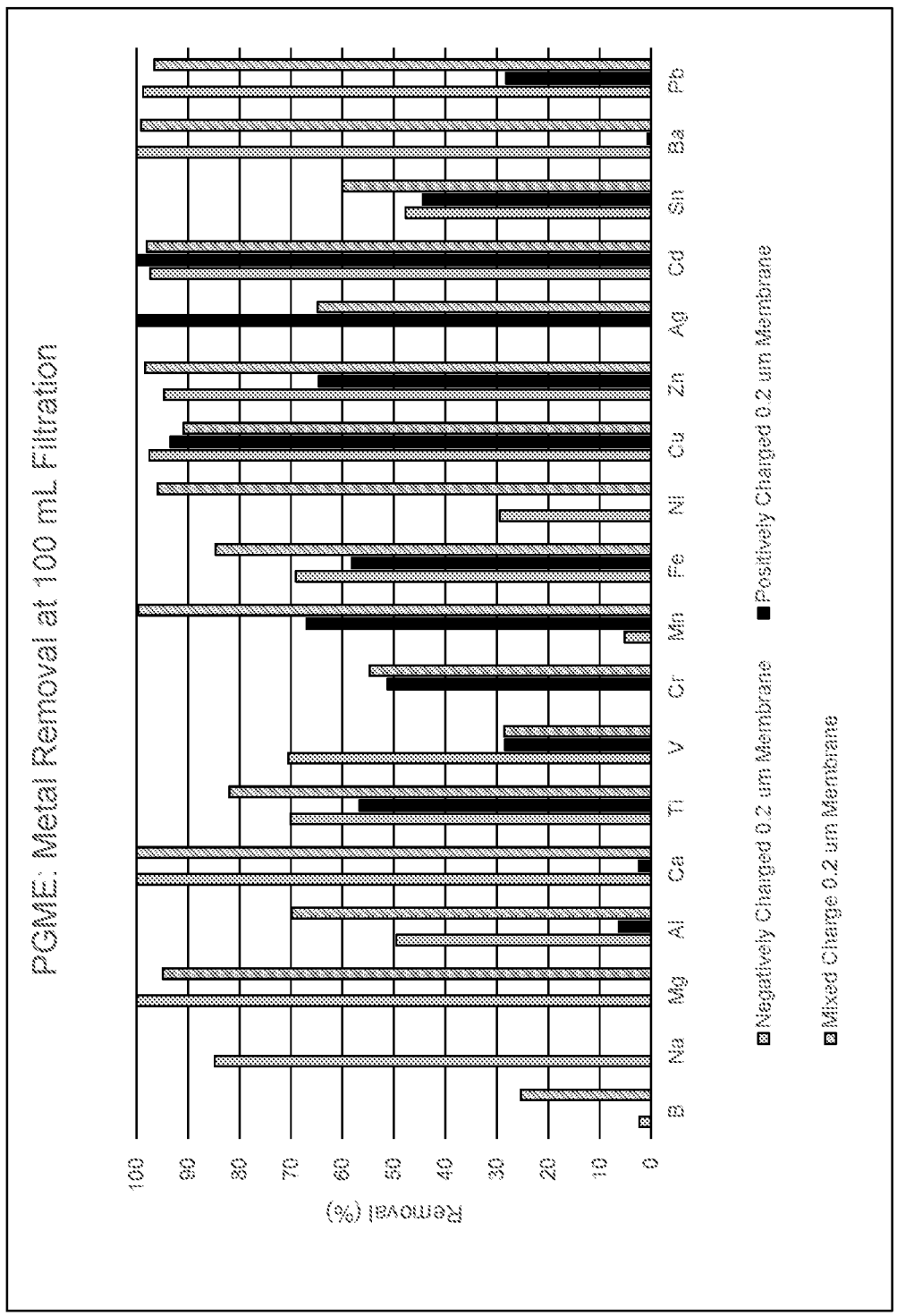
FIG. 13 is a comparative graph of removing metal contaminants from PGME organic liquid showing metals removal by: a porous polymeric membrane with a cross-linked coating comprising a polymerized monomer that is positively charged in the organic liquid; a polymeric membrane with a cross-linked coating comprising a polymerized monomer that is negatively charged in the organic liquid; and a mixed charge membrane with a cross-linked coating comprising a mixture of polymerized monomers some of which are positively charged in the organic liquid and polymerized monomers the rest of which are negatively charged in the organic liquid.

Single Layer Mixed charged 0.2 μm UPE membranes were prepared using a method similar to Example 16 and cut into 47 mm membrane coupons. These membrane coupons were conditioned by washing several times with 10% HCl followed by soaking in 10% HCl overnight and equilibrated with deionized water. For each sample, one 47 mm membrane coupon was secured into a clean PFA 47 mm Single Stage Filter Assembly (Savillex). The membrane and filter assembly were flushed with IPA followed by application solvent. The application solvent was PGME based thinner. The application solvents were spiked with CONOSTAN Oil Analysis Standard S-21 (SCP Science) at a target concentration of 5 ppb of each metal. To determine the filtration metal removal efficiency the metal spiked application solvents were passed through the corresponding 47 mm filter assembly containing each filter at 10 mL/min and the filtrate was collected into a clean PFA jar at 50 mL, 100 mL, and 150 mL. The metal concentration for the metal spiked application solvent and each filtrate sample was determined using ICP-MS. The results are depicted with a comparison to single charged membranes prepared with a similar method in Total Metals Removal (%) in Table 6 and Individual Metal Removal % at 100 mL Filtration in FIG. 13 (PGME). The mixed charge membrane shows improvements in Total Metal Removal when compared to either the positively or negatively single charge membrane. The mixed charged membrane shows improved Individual Metal Removal for at least B, Al, Ti, Mn, Fe, Ni, Sn, when compared to either the positively or negatively single charge membrane.

TABLE 6

| Application Solvent | 0.2 um Membrane | | | | | | | | |
|---|---|---|---|---|---|---|---|---|---|
| | Mixed Charge | | | Negatively Charged PGME | | | Positively Charged | | |
| Filtration Volume (mL) | 50 | 100 | 150 | 50 | 100 | 150 | 50 | 100 | 150 |
| Total Metals Removal (%) | 79.1 | 75.1 | 73.4 | 71.2 | 66.0 | 65.4 | 47.3 | 36.4 | 34.6 |

Example 18

Preparation Negatively Charged Grafted Membrane 47 mm disks of UHMWPE membrane (120 psi HFE bubble point) were wet in 0.5 wt % benzophenone/IPA solution for 25 sec. A grafting monomer solution was made containing 0.6% dimethylacrylamide (DMAM, Sigma) and 0.3% of 2-acrylamido-2-methylpropane sulfonic acid (AMPS, Sigma), 0.15% N,N'-methylenebisacrylamide (MBAM), 3.5% Sodium Sulfate, and 1% sodium persulfate dissolved in water. The grafting monomer solution was placed in a dish and the Benzophenone wetted membrane was introduced into the solution. The dish was covered and the membrane was soaked for 2 minutes. The membrane disk was removed and placed between polyethylene sheets. The excess solution is removed by rolling a rubber roller over the polyethylene/membrane disks/polyethylene sandwich as it lays flat on a table. The polyethylene sandwich is then taped to a transport unit which conveys the assembly through a Fusion Systems broadband UV exposure lab unit emitting at wavelengths from 200 to 600 nm. Time of exposure is controlled by how fast the assembly moves through the UV unit. In this example, the assembly moved through the UV chamber at 9 feet per minute. After emerging from the UV unit, the membrane was removed from the sandwich and immediately placed in DI water, where it was washed by swirling for 5 minutes. Next, it was washed in methanol for 5 minutes. Following this washing procedure the membrane was dried on a holder in an oven operating at 50° C. for 10 min. The resulting membrane had a negative charge which was confirmed with its ability to bind methylene blue dye.

Example 19

Preparation Positively Charged Grafted Membrane 47 mm disks of UHMWPE membrane (90 psi HFE bubble point) were wet in 0.5 wt % benzophenone/IPA solution for 25 sec. A grafting monomer solution was made containing 0.6% dimethylacrylamide (DMAM, Sigma) and 0.3% of acrylamido propyl trimethylammonium chloride (APTAC, Sigma), 0.15% N,N'-methylenebisacrylamide (MBAM), 3.5% Sodium Sulfate, and 1% sodium persulfate dissolved in water. The grafting monomer solution was placed in a dish and the Benzophenone wetted membrane was introduced into the solution. The dish was covered and the membrane was soaked for 2 minutes. The membrane disk was removed and placed between polyethylene sheets. The excess solution is removed by rolling a rubber roller over the polyethylene/membrane disks/polyethylene sandwich as it lays flat on a table. The polyethylene sandwich is then taped to a transport unit which conveys the assembly through a Fusion Systems broadband UV exposure lab unit emitting at wavelengths from 200 to 600 nm. Time of exposure is controlled by how fast the assembly moves through the UV unit. In this example, the assembly moved through the UV chamber at 9 feet per minute. After emerging from the UV unit, the membrane was removed from the sandwich and immediately placed in DI water, where it was washed by swirling for 5 minutes. Next, it was washed in methanol for 5 minutes. Following this washing procedure the membrane was dried on a holder in an oven operating at 50° C. for 10 min. The resulting membrane had a positive charge which was confirmed with its ability to bind Ponceau S dye.

Example 20

Solvent Filtration Experiments: Two Layer Grafted Membrane

Figure 14:
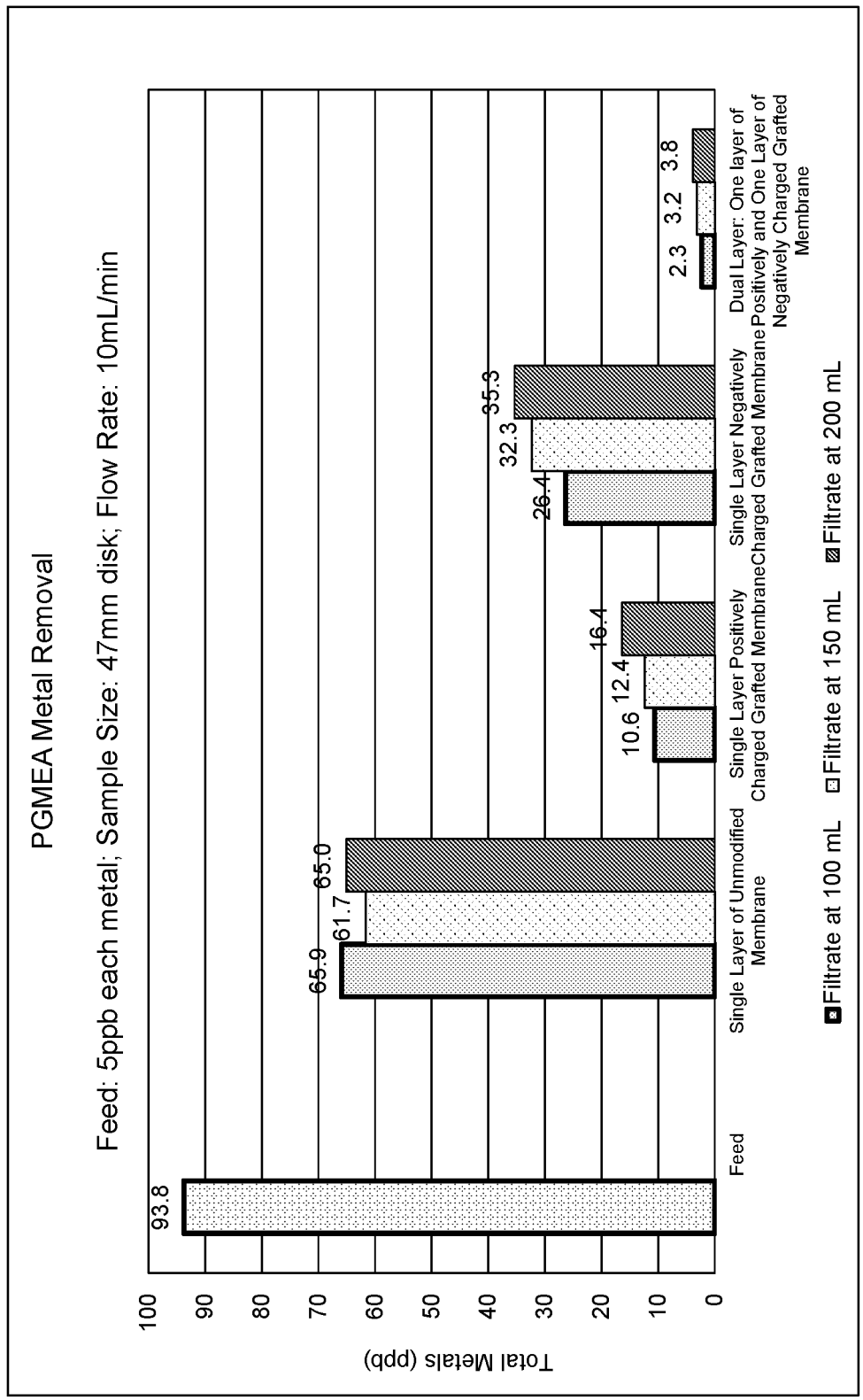
FIG. 14 is a comparative graph of removing metal contaminants from PGMEA organic liquid comparing metals removal from the feed liquid by: the unmodified membrane; a single layer of positively charged grafted membrane; a single layer of negatively charged grafted membrane; and a two layer membrane stack comprising a first layer of positively charged grafted membrane and a second layer of negatively charged grafted membrane.

Positively and Negatively charged UPE membranes were prepared using a grafting method similar to examples 18 and 19 and cut into 47 mm membrane coupons. These membrane coupons were conditioned by washing several times with 10% HCl followed by soaking in 10% HCl overnight and equilibrated with deionized water. For each sample, one 47 mm membrane coupon was secured into a clean PFA 47 mm Single Stage Filter Assembly (Savillex). For another sample one of each positively and negatively charged 47 mm coupon was secured into a clean PFA 47 mm Single Stage Filter Assembly. For another sample one unmodified membrane was secured into a clean PFA 47 mm Single Stage Filter Assembly. The membranes and filter assembly were flushed with IPA followed by application solvent. The application solvent was microelectronics grade PGMEA. The application solvent was spiked with CONOSTAN Oil Analysis Standard S-21 (SCP Science) at a target concentration of 5 ppb of each metal. To determine the filtration metal removal efficiency the metal spiked application solvents were passed through the corresponding 47 mm filter assembly containing each filter at 10 mL/min and the filtrate was collected into a clean PFA jar at 100 mL, 150 mL, and 200 mL. The metal concentration for the metal spiked application solvent and each filtrate sample was determined using ICP-MS. The results were depicted in Total Metals Removal (%) in FIG. 14 (PGMEA).

The following clauses define particular aspects and embodiments of the invention.

Clause 1. A method of removing metal contaminants from an organic liquid used for photoresist, the method comprising: passing a photoresist organic liquid through a porous polymeric membrane comprising a coating, the coating comprising a cross-linked polymerized monomer with a positive charge; and, removing metals contaminants from the organic liquid wherein the organic liquid used for photoresist has a lower concentration of the metal contaminants after passing through the porous membrane.

Clause 2. The method of clause 1, wherein the polymerized monomer comprising a positive charge in the organic liquid comprises a monomer that is selected from a group consisting of 2-(dimethylamino)ethyl hydrochloride acrylate, [2-(acryloyloxy)ethyl]trimethylammonium chloride, 2-aminoethyl methacrylate hydrochloride, N-(3-aminopropyl) methacrylate hydrochloride, 2-(dimethylamino)ethyl methacrylate hydrochloride, [3-(methacryloylamino)propyl]trimethylammonium chloride solution, [2-(methacryloyloxy) ethyl]trimethylammonium chloride, acrylamidopropyl trimethylammonium chloride, 2-aminoethyl methacrylamide hydrochloride, N-(2-aminoethyl) methacrylamide hydrochloride, N-(3-aminopropyl)-methacrylamide hydrochloride, diallyldimethylammonium chloride, allylamine hydrochloride, vinyl imidazolium hydrochloride, vinyl pyridinium hydrochloride, and vinyl benzyl trimethyl ammonium chloride.

Clause 3. The method of clause 1, wherein the polymerized monomer comprising a positive charge in the organic liquid comprises acrylamido propyl trimethylammonium chloride (APTAC).

Clause 4. The method of clause 1, wherein the coating further comprises a polymerized monomer with a negative charge in the organic liquid, the monomer selected from a group consisting of 2-ethylacrylic acid, acrylic acid, 2-carboxyethyl acrylate, 3-sulfopropyl acrylate potassium salt, 2-propyl acrylic acid, 2-(trifluoromethyl)acrylic acid, methacrylic acid, 2-methyl-2-propene-1-sulfonic acid sodium salt, mono-2-(methacryloyloxy)ethyl maleate, and 3-sulfopropyl methacrylate potassium salt, 2-acrylamido-2-methyl-1-propanesulfonic acid, 3-methacrylamido phenyl boronic acid, vinyl sulfonic acid, and vinyl phosphonic acid.

Clause 5. The method of clause 1, wherein the monomer comprising a positive charge is a zwitterion.

Clause 6. A method of removing metal contaminants from an organic liquid comprising: passing an organic liquid through a porous polymeric membrane comprising a coating having a cross-linked polymerized monomer with a positive charge in the organic liquid and removing metals contaminants from the organic liquid; and passing the organic liquid through a porous polymeric membrane comprising a coating having a cross-linked polymerized monomer with a negative charge in the organic liquid and removing metals contaminants from the organic liquid.

Clause 7. A method of removing metal contaminants from an organic liquid comprising: passing the organic liquid through a porous polymeric membrane comprising a coating having cross-linked polymerized monomers with positive and negative charges; and wherein the organic liquid has a lower concentration of the metal contaminants after passing through the porous membrane.

Clause 8. The method as in any one of the preceding clauses, in which the organic liquid comprises one or more solvents selected from the group consisting of methyl-amyl ketone, ethyl-3-ethoxypropionate, propylene glycol methyletheracetate, methanol, ethyl lactate, Methyl isobutyl carbinol, N-butyl acetate, Methyl-2-hydroxyisobutyrate, cyclohexanone, and propylene glycol methyl ether.

Clause 9. The method as in any one of the preceding clauses, in which the coating is grafted to the porous polymeric membrane.

Clause 10. The method as in any one of the preceding clauses, in which the one or more charged membrane has a charge density of from about 0.5 to about 20 meq/m$^2$.

Clause 11. The method as in any one of the preceding clauses, in which the porous polymeric membrane is selected from a group consisting of a polyethylene containing porous membrane, a polysulfone containing porous membrane, and a halocarbon containing porous membrane.

Clause 12. The method as in any one of the preceding clauses, in which the porous polymeric membrane comprises a polyolefin.

Clause 13. The method as in any one of the preceding clauses, wherein the metal contaminants are selected from the group consisting of Al, Ca, Cr, Cu, Fe, Pb, Mg, Mn, Ni, K, Na, Sn, Ti, and Zn.

Clause 14. The method as in any one of the preceding clauses wherein the metal contaminants are selected from the group consisting of Al, Cr, Cu, Fe, Pb, Mg, Ni, Na, Sn, Ti, and Zn.

Clause 15. The method as in any one of the preceding clauses, wherein the metal contaminants are selected from the group consisting of Fe, Ni, Cr, Cu, and Al.

Clause 16. The method as in any one of the preceding clauses, wherein the metal contaminants are selected from the group consisting of Fe, Ni, and Cr.

Clause 17. The method as in any one of the preceding clauses, wherein the concentration of metal contaminants in the organic liquid used for photoresist after passing through the porous membrane is less than about 20 ppb.

Clause 18. The method as in any one of the preceding clauses, wherein the concentration of Fe contaminants in the organic liquid used for photoresist after passing through the porous membrane is less than about 0.7 ppb.

Clause 19. The method as in any one of the preceding clauses, wherein the concentration of Cr contaminants in the organic liquid used for photoresist after passing through the porous membrane is less than about 2.0 ppb.

Clause 20. The method as in any one of the preceding clauses, wherein the concentration of Al contaminants in the organic liquid used for photoresist after passing through the porous membrane is less than about 0.5 ppb.

Clause 21. A filtration device comprising: a first porous polymeric membrane comprising a coating having a cross-linked polymerized monomer with a positive charge and a second porous polymeric membrane comprising a coating having a cross-linked polymerized monomer with a negative charge.

Clause 22. A filtration device comprising: a porous polymeric membrane comprising a coating having cross-linked polymerized monomers with positive charges and cross-linked polymerized monomers with negative charges.

Clause 23. The filtration device of clause 21 or 22, wherein the monomer with a positive charge is selected from a group consisting of 2-(dimethylamino)ethyl hydrochloride acrylate, [2-(acryloyloxy)ethyl]trimethylammonium chloride, 2-aminoethyl methacrylate hydrochloride, N-(3-aminopropyl) methacrylate hydrochloride, 2-(dimethylamino)ethyl methacrylate hydrochloride, [3-(methacryloylamino)propyl]trimethylammonium chloride solution, [2-(methacryloyloxy)ethyl]trimethylammonium chloride, acrylamidopropyl trimethylammonium chloride, 2-aminoethyl methacrylamide hydrochloride, N-(2-aminoethyl) methacrylamide hydrochloride, N-(3-aminopropyl)-methacrylamide hydrochloride, diallyldimethylammonium chloride, allylamine hydrochloride, vinyl imidazolium hydrochloride, vinyl pyridinium hydrochloride, and vinyl benzyl trimethyl ammonium chloride.

Clause 24. The filtration device as in any one of clauses 21-23, wherein the monomer with a positive charge comprises acrylamido propyl trimethylammonium chloride (APTAC).

Clause 25. The filtration device as in any one of clauses 21-24, wherein the polymerized monomer with a negative charge comprise a monomer with negative charge selected from a group consisting of 2-ethylacrylic acid, acrylic acid, 2-carboxyethyl acrylate, 3-sulfopropyl acrylate potassium salt, 2-propyl acrylic acid, 2-(trifluoromethyl)acrylic acid, methacrylic acid, 2-methyl-2-propene-1-sulfonic acid sodium salt, mono-2-(methacryloyloxy)ethyl maleate, and 3-sulfopropyl methacrylate potassium salt, 2-acrylamido-2-methyl-1-propanesulfonic acid, 3-methacrylamido phenyl boronic acid, vinyl sulfonic acid, and vinyl phosphonic acid.

Clause 26. The filtration device as in any one of clauses 21-25, wherein the monomer with negative charge comprises sulfonic acid.

Clause 27. The filtration device as in any one of clauses 21-26, in which the coating is grafted to the porous polymeric membrane.

Clause 28. The filtration device as in any one of clauses 21-27, in which the one or more of the charged membranes has a charge density of from about 0.5 to about 20 meq/m$^2$.

Clause 29. The filtration device as in any one of clauses 21-28, in which the porous polymeric membrane is selected from a group consisting of a polyethylene containing porous membrane, a polysulfone containing membrane, and a halocarbon containing porous membrane.

Clause 30. The filtration device as in any one of clauses 21-29, in which the porous polymeric membrane comprises a polyolefin.

Clause 31. A porous polymeric membrane comprising: a coating comprising cross-linked polymerized monomers; said polymerized monomer comprising a positive charge in an organic liquid.

Clause 32. The porous polymeric membrane of clause 31, wherein the monomer comprising a positive charge in the organic liquid is selected from a group consisting of 2-(dimethylamino)ethyl hydrochloride acrylate, [2-(acryloyloxy)ethyl]trimethylammonium chloride, 2-aminoethyl methacrylate hydrochloride, N-(3-aminopropyl) methacrylate hydrochloride, 2-(dimethylamino)ethyl methacrylate hydrochloride, [3-(methacryloylamino)propyl]trimethylammonium chloride solution, [2-(methacryloyloxy)ethyl]trimethylammonium chloride, acrylamidopropyl trimethylammonium chloride, 2-aminoethyl methacrylamide hydrochloride, N-(2-aminoethyl) methacrylamide hydrochloride, N-(3-aminopropyl)-methacrylamide hydrochloride, diallyldimethylammonium chloride, allylamine hydrochloride, vinyl imidazolium hydrochloride, vinyl pyridinium hydrochloride, and vinyl benzyl trimethyl ammonium chloride.

Clause 33. The porous polymeric membrane as in any one of clauses 31-32, wherein the monomer comprising a positive charge is a zwitterionic monomer.

Clause 34. The porous polymeric membrane as in any one of clauses 31-33, in which the coating is grafted to the porous polymeric membrane.

Clause 35. The porous polymeric membrane as in any one of clauses 31-34, in which the one or more of the charged membranes has a charge density of from about 0.5 to about 20 meq/m$^2$.

Clause 36. The porous polymeric membrane as in any one of clauses 31-35, in which the porous polymeric membrane is selected from a group consisting of a polyethylene containing porous membrane, a polysulfone containing membrane, and a halocarbon containing porous membrane.

Clause 37. The porous polymeric membrane as in any one of clauses 31-36, in which the porous polymeric membrane comprises a polyolefin.

Clause 38. The porous polymeric membrane as in any one of clauses 31-37, in which the one or more coated porous polymeric membranes secured to a filter housing that has a liquid inlet and a liquid outlet.

Clause 39. The porous polymeric membrane as in anyone of clauses 31-38, in which the zwitterionic momoner is selected from the group consisting of [3-(Methacryloylamino)propyl]dimethyl(3-sulfopropyl)ammonium hydroxide, [2-(Methacryloyloxy)ethyl]dimethyl-(3-sulfopropyl) ammonium hydroxide, 2-(Methacryloyloxy)ethyl 2-(Trimethylammonio)ethyl Phosphate, and 1-(3-Sulfopropyl)-2-vinylpyridinium hydroxide.

Clause 40. A porous membrane comprising: a coating having a cross-linked polymerized monomer comprising a negative charge in an organic liquid.

Clause 41. The porous membrane of clause 40 wherein the polymerized monomer with a negative charge in the organic liquid comprises a momoner selected from a group consisting of 2-ethylacrylic acid, acrylic acid, 2-carboxyethyl acrylate, 3-sulfopropyl acrylate potassium salt, 2-propyl acrylic acid, 2-(trifluoromethyl)acrylic acid, methacrylic acid, 2-methyl-2-propene-1-sulfonic acid sodium salt, mono-2-(methacryloyloxy)ethyl maleate, and 3-sulfopropyl methacrylate potassium salt, 2-acrylamido-2-methyl-1-propanesulfonic acid, 3-methacrylamido phenyl boronic acid, vinyl sulfonic acid, and vinyl phosphonic acid.

Clause 42. The porous membrane having a coating comprising a cross-linked polymerized monomer with a charge as in any one of preceding clauses, the dye binding capacity of the membrane decreases by less than 20 percent after an overnight Soxhlet extraction in isopropyl alcohol.

Clause 43. The porous membrane having a coating comprising a cross-linked polymerized monomer with a negative charge as in any one of preceding clauses, the dye binding capacity of the membrane as determined by Methylene blue dye binding, as disclosed herein, ranges from 10 µg/cm$^2$ to 50 µg/cm$^2$.

Clause 44. The porous membrane having a coating comprising a cross-linked polymerized monomer with a positive charge as in any one of preceding clauses, the dye binding capacity of the membrane as determined by Ponceau-S dye dye binding, as disclosed herein, ranges from 10 µg/cm$^2$ to 80 µg/cm$^2$.

Approximating language, as used herein throughout the specification and claims, may be applied to modify any quantitative or qualitative representation that could permissibly vary without resulting in a change in the basic function to which it is related. Accordingly, a value modified by a term such as "about" or numerical ranges is not to be limited to a specified precise value, and may include values that differ from the specified value. In at least some instances, the approximating language may correspond to the precision of an instrument for measuring the value. Furthermore, "removing or reducing metal contaminants" may be used in combination with a term, and include a varying amount of metal ion removal and is not to be limited to a specified precise value, and may include values that differ from a specified value.

It will be apparent to those skilled in the art that various modifications and variations can be made in the method and system of the present disclosure without departing from the spirit or scope of the disclosure. Thus, it is intended that the present disclosure include modifications and variations that are within the scope of the appended claims and their equivalents.

While the disclosure has been described in detail in connection with only a limited number of aspects and embodiments, it should be understood that the disclosure is not limited to such aspects. Rather, the disclosure can be modified to incorporate any number of variations, alterations, substitutions, or equivalent arrangements not heretofore described, but which are commensurate with the scope of the claims. Additionally, while various embodiments of the disclosure have been described, it is to be understood that aspects of the disclosure may include only some of the described embodiments. Accordingly, the disclosure is not to be seen as limited by the foregoing description, but is only limited by the scope of the appended claims.

What is claimed is:

1. A coated porous polymeric membrane comprising a porous polymeric membrane having a polymer coating on surfaces thereof, wherein the polymer coating is cross-linked and not grafted to the porous polymeric membrane surfaces and has a polymerized monomer comprising a positive charge in an organic liquid,
    wherein the coating is cross-linked with a cross-linking agent selected from the group consisting of 1,6-hexanediol diacrylate, tetraethylene glycol diacrylate, 1,1,1-trimethylolpropane triacrylate, and combinations thereof and
    wherein the porous polymeric membrane is a polyolefin membrane having a bubble point, measured from the pressure required to displace ethoxy-nonafluorobutane through pores of the porous polymeric membrane, in a range of 4-160 psi.

2. The porous membrane of claim 1, wherein the monomer comprising the positive charge in the organic liquid is selected from a group consisting of 2-(dimethylamino)ethyl hydrochloride acrylate, [2-(acryloyloxy)ethyl]trimethylammonium chloride, 2-aminoethyl methacrylate hydrochloride, N-(3-aminopropyl) methacrylate hydrochloride, 2-(dimethylamino)ethyl methacrylate hydrochloride, [3-(methacryloylamino)propyl] trimethylammonium chloride solution, [2-(methacryloyloxy)ethyl]trimethylammonium chloride, acrylamidopropyl trimethylammonium chloride, 2-aminoethyl methacrylamide hydrochloride, N-(2-aminoethyl) methacrylamide hydrochloride, N-(3-aminopropyl)-methacrylamide hydrochloride, diallyldimethylammonium chloride, allylamine hydrochloride, vinyl imidazolium hydrochloride, vinyl pyridinium hydrochloride, and vinyl benzyl trimethyl ammonium chloride.

3. The porous membrane of claim 1, wherein the monomer comprising the positive charge in the organic liquid comprises acrylamido propyl trimethylammonium chloride (APTAC).

4. The porous membrane of claim 1, wherein the monomer comprising the positive charge in the organic liquid is a zwitterion.

5. A filtration device comprising: a first coated porous polymeric membrane comprising a first porous polymeric membrane having a polymer coating on surfaces thereof, wherein the polymer coating is cross-linked and not grafted to the first porous polymeric membrane surfaces and has a polymerized monomer with a positive charge in an organic liquid, and a second coated porous polymeric membrane comprising a second porous polymeric membrane having a polymer coating on surface thereof, wherein the polymer coating is cross-linked and not grafted to the second porous polymeric surfaces and has a polymerized monomer with a negative charge in the organic liquid,
    wherein the coating is cross-linked with a cross-linking agent selected from the group consisting of 1,6-hexanediol diacrylate, tetraethylene glycol diacrylate, 1,1,1-trimethylolpropane triacrylate, and combinations thereof and
    wherein the first porous polymeric membrane or the second porous polymeric membrane is a polyolefin membrane having a bubble point, measured from the pressure required to displace ethoxy-nonafluorobutane through pores of the porous polymeric membrane, in a range of 4-160 psi.

6. The filtration device of claim 5, in which the monomer comprising the positive charge in the organic liquid is selected from a group consisting of 2-(dimethylamino)ethyl hydrochloride acrylate, [2-(acryloyloxy)ethyl]trimethylammonium chloride, 2-aminoethyl methacrylate hydrochloride, N-(3-aminopropyl) methacrylate hydrochloride, 2-(dimethylamino)ethyl methacrylate hydrochloride, [3-(methacryloylamino)propyl] trimethylammonium chloride solution, [2-(methacryloyloxy)ethyl]trimethylammonium chloride, acrylamidopropyl trimethylammonium chloride, 2-aminoethyl methacrylamide hydrochloride, N-(2-aminoethyl) methacrylamide hydrochloride, N-(3-aminopropyl)-methacrylamide hydrochloride, diallyldimethylammonium chloride, allylamine hydrochloride, vinyl imidazolium hydrochloride, vinyl pyridinium hydrochloride, and vinyl benzyl trimethyl ammonium chloride.

7. The filtration device of claim 5, in which the monomer comprising the negative charge in the organic liquid is selected from a group consisting of 2-ethylacrylic acid, acrylic acid, 2-carboxyethyl acrylate, 3-sulfopropyl acrylate potassium salt, 2-propyl acrylic acid, 2-(trifluoromethyl) acrylic acid, methacrylic acid, 2-methyl-2-propene-1-sulfonic acid sodium salt, mono-2-(methacryloyloxy)ethyl maleate, and 3-sulfopropyl methacrylate potassium salt, 2-acrylamido-2-methyl-1-propanesulfonic acid, 3-methacrylamido phenyl boronic acid, vinyl sulfonic acid, and vinyl phosphonic acid.

8. The porous membrane of claim 1, wherein said coating further comprises polymerized monomers with negative charges.

9. The porous membrane of claim 8, wherein the monomer with a positive charge is selected from a group consisting of 2-(dimethylamino)ethyl hydrochloride acrylate, [2-(acryloyloxy)ethyl]trimethylammonium chloride, 2-aminoethyl methacrylate hydrochloride, N-(3-aminopropyl) methacrylate hydrochloride, 2-(dimethylamino)ethyl methacrylate hydrochloride, [3-(methacryloylamino)propyl] trimethylammonium chloride solution, [2-(methacryloyloxy)ethyl]trimethylammonium chloride, acrylamidopropyl trimethylammonium chloride, 2-aminoethyl methacrylamide hydrochloride, N-(2-aminoethyl) methacrylamide hydrochloride, N-(3-aminopropyl)-methacrylamide hydrochloride, diallyldimethylammonium chloride, allylamine hydrochloride, vinyl imidazolium hydrochloride, vinyl pyridinium hydrochloride, and vinyl benzyl trimethyl ammonium chloride.

10. The porous membrane of claim 8, wherein the monomer with a negative charge is selected from a group consisting of 2-ethylacrylic acid, acrylic acid, 2-carboxyethyl acrylate, 3-sulfopropyl acrylate potassium salt, 2-propyl acrylic acid, 2-(trifluoromethyl)acrylic acid, methacrylic acid, 2-methyl-2-propene-1-sulfonic acid sodium salt, mono-2-(methacryloyloxy)ethyl maleate, and 3-sulfopropyl methacrylate potassium salt, 2-acrylamido-2-methyl-1-propanesulfonic acid, 3-methacrylamido phenyl boronic acid, vinyl sulfonic acid, and vinyl phosphonic acid.

11. The porous polymeric membrane of claim 1, wherein the polyolefin membrane is an ultra-high molecular weight polyethylene membrane.

12. The porous membrane of claim 1, wherein the monomer comprising the positive charge in the organic liquid is selected from a group consisting of 2-(dimethylamino)ethyl hydrochloride acrylate, [2-(acryloyloxy)ethyl]trimethylammonium chloride, 2-aminoethyl methacrylate hydrochloride, N-(3-aminopropyl) methacrylate hydrochloride, 2-(dimethylamino)ethyl methacrylate hydrochloride, [3-(methacryloylamino)propyl] trimethylammonium chloride solution, [2-(methacryloyloxy)ethyl]trimethylammonium chloride, acrylamidopropyl trimethylammonium chloride, diallyldimethylammonium chloride, allylamine hydrochloride, vinyl imidazolium hydrochloride, vinyl pyridinium hydrochloride, and vinyl benzyl trimethyl ammonium chloride.

13. The filtration device of claim 5, wherein the monomer comprising the positive charge in the organic liquid is selected from a group consisting of 2-(dimethylamino)ethyl hydrochloride acrylate, [2-(acryloyloxy)ethyl]trimethylammonium chloride, 2-aminoethyl methacrylate hydrochloride, N-(3-aminopropyl) methacrylate hydrochloride, 2-(dimethylamino)ethyl methacrylate hydrochloride, [3-(methacryloylamino)propyl] trimethylammonium chloride solution, [2-(methacryloyloxy)ethyl]trimethylammonium chloride, acrylamidopropyl trimethylammonium chloride, diallyldimethylammonium chloride, allylamine hydrochloride, vinyl imidazolium hydrochloride, vinyl pyridinium hydrochloride, and vinyl benzyl trimethyl ammonium chloride.

* * * * *